United States Patent [19]
Greene et al.

[11] Patent Number: 5,533,383
[45] Date of Patent: Jul. 9, 1996

[54] INTEGRATED ACOUSTIC LEAK DETECTION PROCESSING SYSTEM

[75] Inventors: David A. Greene; Rosemary A. Greene, both of San Jose; Donald C. Gaubatz, Cupertino, all of Calif.

[73] Assignee: General Electric Company, San Jose, Calif.

[21] Appl. No.: 292,656

[22] Filed: Aug. 18, 1994

[51] Int. Cl.$^6$ .......................... G01M 3/24; G21C 17/007
[52] U.S. Cl. .......................... 73/40.5 A; 73/587; 364/550; 364/507; 376/252; 395/22
[58] Field of Search .............................. 73/40.5 A, 587, 73/592; 376/250, 251, 252; 395/22; 364/507, 550

[56] References Cited

U.S. PATENT DOCUMENTS

| | | | |
|---|---|---|---|
| 3,822,586 | 7/1974 | Pollock | 73/587 |
| 3,858,439 | 1/1975 | Nakamura | 73/587 |
| 4,033,179 | 7/1977 | Romrell | 73/587 |
| 4,181,027 | 1/1980 | Talbott, Jr. | 73/665 |
| 4,570,489 | 2/1986 | Baumaire et al. | 73/658 |
| 4,640,121 | 2/1987 | Leuker et al. | 73/40.5 A |
| 4,901,575 | 2/1990 | Bohannan et al. | 73/587 |
| 4,979,124 | 12/1990 | Sachse et al. | 73/587 |
| 5,046,019 | 9/1991 | Basehore | 395/22 |
| 5,247,584 | 9/1993 | Krogmann | 395/22 |
| 5,257,545 | 11/1993 | Au–Yang | 73/597 |
| 5,270,950 | 12/1993 | Conley et al. | 73/587 |
| 5,361,636 | 11/1994 | Farstad et al. | 73/40.5 A |

FOREIGN PATENT DOCUMENTS

| | | | |
|---|---|---|---|
| 52-38284 | 3/1977 | Japan | 73/40.5 A |
| 214636 | 9/1988 | Japan | 73/592 |
| 204031 | 7/1992 | Japan | 73/40.5 A |
| 157662 | 6/1993 | Japan . | |
| 217446 | 8/1994 | Japan . | |
| 1657995 | 6/1991 | U.S.S.R. | 73/40.5 A |

OTHER PUBLICATIONS

Cox, E., "Integrating Fuzzy Logic into Neural Networks", AI Expert, Jun. 1992, pp. 43–47.
Ungar, L. H. et al., "Adaptive Networks For Fault Diagnosis and Process Control," Computers Chem. Engng, vol. 14, No. 4/5, Dec. 1990, pp. 561–572.
Zwingelstein, G. et al., "Applications of Expert Systems and Neural Networks For the Condition Monitoring and Inspection of French Nulcear Power Plants", Proceedings of the American Power Conference, Dec. 1990, pp. 895–900.

*Primary Examiner*—Hezron E. Williams
*Assistant Examiner*—Daniel S. Larkin
*Attorney, Agent, or Firm*—James E. McGinness

[57] ABSTRACT

A system for mapping absolute acoustic noise intensity in a three-dimensional acoustic noise field, and using three-dimensional absolute noise intensities to infer operational or performance characteristics of components or structures within the monitored field. Localized noise sources are extracted using a distant array of transducers, and the absolute intensity can be measured even when totally masked by background noise at the transducer locations. The system includes an integrated sensor installation; a neural network detection system algorithm; a zoom system to precisely examine a small region in the steam generator vessel; a fuzzy logic system detection algorithm; and an expert detection system. The signal processing subsystem operates at three different levels of detection. At the top level of detection a trained neural network system monitors the vessel length for any indication of a leak. The proposed approach uses discriminators which do not require any beamforming of the sensor signals. The presence of a leak and the general location in the vessel is determined using a fuzzy logic expert system. The leak indications are passed to a second level of detection: a beamformed system which will monitor the indicated portion of the vessel. A third level of detection systematically monitors the tagged locations to determine if a leak is really present, remaining on the specific locations to detect a leak above the defined threshold to a high degree of accuracy. The actions to be taken will be controlled by a second fuzzy logic expert interface controller.

20 Claims, 10 Drawing Sheets

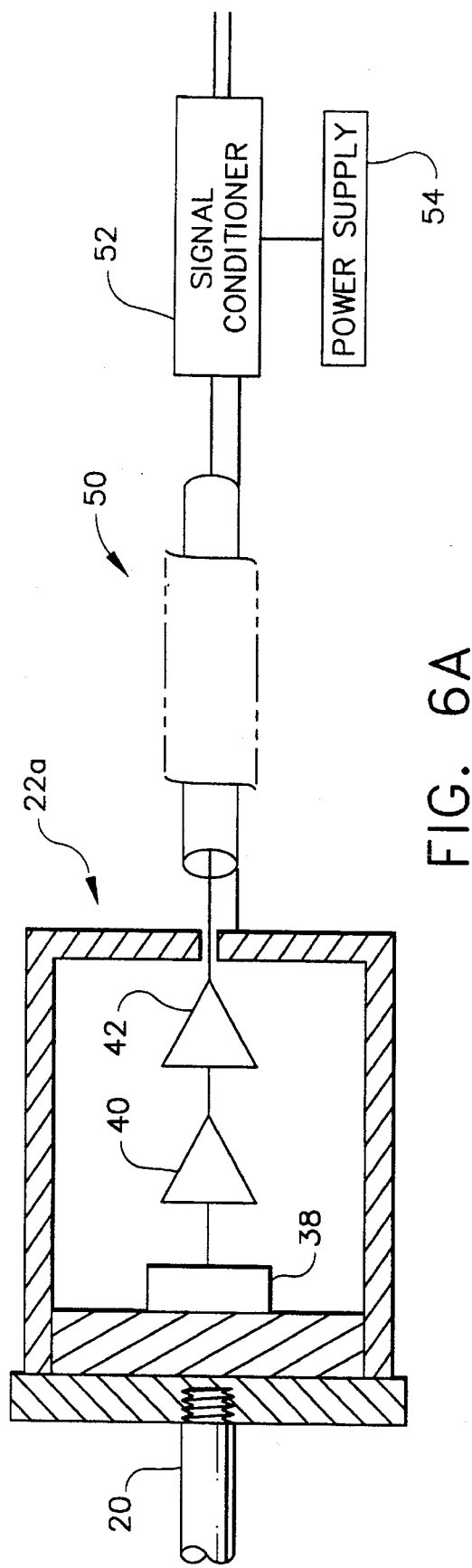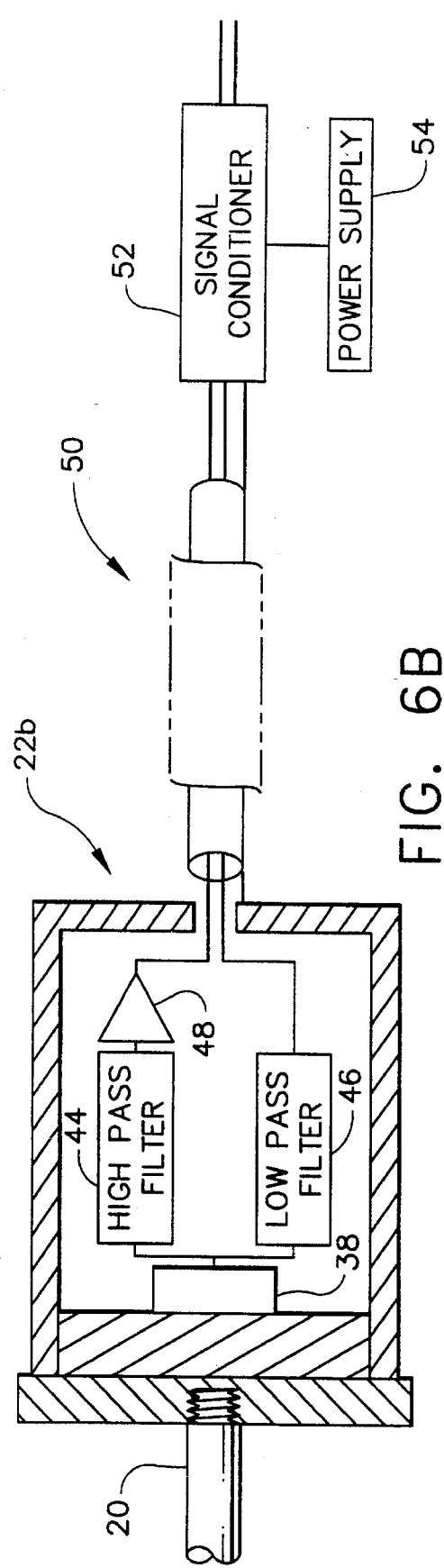

INTEGRATED ACOUSTIC LEAK DETECTION PROCESSING SYSTEM

FIELD OF THE INVENTION

This invention generally relates to mapping of absolute acoustic noise intensity in a three-dimensional acoustic noise field and to use of three-dimensional absolute noise intensities to infer operational or performance characteristics of components or structures within the monitored field. Localized noise sources are extracted using a distant array of transducers, and the absolute intensity can be measured even when totally masked by background noise at the transducer locations. In particular, the invention relates to nondestructive examination of the steam generator of a liquid metal (sodium) fast breeder reactor (LMFBR), and to inferring failure of the boundary between the water and sodium circuits by a three-dimensional mapping of the absolute acoustic noise field within the steam generator to detect and locate the breach.

BACKGROUND OF THE INVENTION

Hot liquid metal (sodium) flows on the shell side of a typical LMFBR steam generator, and high-pressure water/steam flows through the internal tube bundle in counterflow to the sodium. When the barrier between the sodium and water circuits is defective, a localized sodium-water reaction occurs at the site of the defect. The sodium and water reaction and growth of the reaction product (hydrogen gas) bubbles produces a localized noise source within the vessel. The leak site is stationary or fixed in space. The random acoustic pressures generated by the sodium-water reaction can be monitored to assess whether a leak exists at a given location within the vessel, and if it exists, to predict the magnitude and damage potential of the leak.

Operational experience with LMFBR power plants has shown the steam generator to be the prime component having potential to reduce plant availability. Data from sodium-water reaction damage investigations show any through-wall hole in a steam generator heat transfer tube can cause severe damage to the unit, unless corrective action is taken to prevent damage propagation. As shown in FIG. 1, experimental evidence indicates this corrective action must be taken within 40 sec from initiation of an intermediate-sized leak. This timescale is too short for effective operator intervention. Such a requirement can only be satisfied by an automatic shutdown system for the steam generator activated by suitable leak detection systems.

The advanced liquid metal reactor (ALMR) includes liquid sodium-heated, helical coil steam generators 2 (see FIG. 2) producing superheated steam to drive the turbines 4. The steam generator is designed to be convectively cooled by blowing cold air between the steam generator shell 6 and the outer shroud 8. A reaction product separation tank 10 and hydrogen vent system 12 protect the secondary heat transfer system in the event of a sodium-water reaction in the steam generator. The vessel is designed with rupture disks 14 that drain the sodium from the steam generator into tank 10, thereby protecting against damage to the intermediate loop and the reactor.

A sodium-water reaction in the steam generator results from failure of the barrier between the sodium and steam/water circuits. Failures can range from a microscopically small defect in a single tube injecting less than about 1 gm/sec of water (small leak), to a relatively large hole in a single tube injecting about 100 gm/sec of water (intermediate leak), or to complete failure of one or more heat transfer tubes so that the injection rate can reach thousands of gm/sec for a short period of time (large leak). Water/steam injection can also result from failure of the tube sheet, again with the potential for a wide range of injection rates.

Reference designs for the ALMR secondary heat transfer system, and specifically for the steam generator, include features to accommodate sodium-water reactions and reduce any potential for damage propagation to other parts of the reactor system to a negligible level. The normal progression of an intermediate or large sodium-water reaction event in a steam generator will cause a rise in steam generator pressure from the normal level. A burst tube can cause failure of the rupture disk 14 (see FIG. 2) within about 10 μsec; smaller leaks cause a gradual over-pressurization and disk failure at 2 MPa. Over-pressurization of the unit causes failure of the rupture disks located at the base of the unit, and activation of the steam/water isolation and blowdown system. The steam generator protection system will isolate and blow down the water side within 30 seconds of the rupture disk failure, and reaction products are passively vented through the failed disk. The reaction products are gravity drained into a specially designed reaction product collection tank, and gaseous hydrogen is burned to form steam before release to the atmosphere. The secondary loop has very low levels of reactivity so there is insignificant reactivity release beyond the plant boundary.

Water seepage through a defect in the heat transfer tube of a sodium heated steam generator causes self-enlargement of the original fissure. The damage initially takes the form of a crater on the sodium side connected to the water side by the original fissure. While the crater is deepening, the water/steam injection through the fissure is limited by choked flow, and is a function of the original fissure minimum area. This phenomenon is referred to as "self-wastage". When the crater finally deepens and breaks through to the water side of the tube, the injection rate escalates orders of magnitude, into a leak rate classified as an "intermediate" regime. If the original defect is sufficiently large in size (a few mils), a free-standing jet of water/steam (fractional to a few grams per second) is injected into the sodium. The small leak jet reacts to produce high-temperature, extremely corrosive reaction products which impinge onto adjacent tubes. These products cause wastage of the tube and eventually failure of the tube. The resultant water injection rate is generally in the intermediate regime (10 gm/sec to 1 kg/sec of water/steam). Escalation can occur within a few (>3) seconds. Further escalation of damage due to wastage, or from tube overheating and bursting, results in injection rates in excess of hundreds of grams per second, classified as "large" regime. Escalation time scales are again of the order of a few tens of seconds.

Both microleaks and small leaks propagate into intermediate-sized leaks, the microleak without warning and the small leak with an ambiguous indication at best. Test and operating plant incidents showed intermediate leaks cause maximum damage to a steam generator system. A systematic series of tests also showed that the acoustic signal from such leaks could be reliably detected, and automatic corrective actions taken in time to prevent any further damage propagation. Chemical detection may provide similar protection at high sodium flow rates, but if the transit time from the leak site to the detector is greater than 30 seconds, it becomes ineffective for intermediate leak protection. Many operating conditions result in transit times greater than this, and so the chemical detection system will have limited coverage.

Water/steam injection through the fissure is not always constant, and for significant periods of time, a microleak may remain plugged. The intermittent character of the injection and the long time scales associated with microleak phenomena reduce the reliability of leak detection prior to leak escalation. The actual time taken for the leak to transition from slow water seepage to an intermediate leak is an important parameter in designing water-into-sodium leak detection and protection systems. If the escalation time is of the order of 20 minutes or longer, the reactor operator can take corrective action to prevent damage propagation. If the time scale is less than about 2 minutes, the operator cannot react quickly enough and an automatic protection system is required. Such systems require confirming evidence that a leak is present, to reduce the possibility of false alarms and reduced plant availability. One candidate for the automatic protection system is chemical monitoring for reaction products. The transit time from a leak site to the chemical monitor at full power is of the order of minutes. The demonstrated escalation time of a few seconds indicates the utility of chemical monitors, even at full sodium flow conditions, is questionable for protection against escalating damage.

When the injection rate of water/steam into sodium is very low, i.e., microleaks up to about 0.01 gm/sec, any leak detection system is ineffective. The hydrogen released by the reaction or the acoustic noise of the reaction is so small that it is masked by normal background fluctuations in the parameters. Initial defect sizes are below a practical limit for detection/location by non-destructive examination (NDE) techniques.

It is essential that the power plant operator and steam generator designer have sufficient knowledge of wastage phenomena, and its consequences, to judge the action required from the behavior of leak detection monitors. The extreme sensitivity of detection systems increases the potential for false alarms and reduced plant availability. Alarm levels must be set to provide protection while minimizing detection errors. If the level is set too high, then damage propagation to large leak conditions will occur. If the level is set too low, then spurious power plant shutdowns will reduce availability, and ultimately plant reliability, since each rapid shutdown exposes equipment to thermal and mechanical transients and shocks.

The majority of leak detection systems designed and incorporated into currently operating steam generator systems have attempted to detect the smallest possible leak. Corrective action is usually initiated by warning the plant operator when an anomalous signal is present. Some form of automatic shutdown of the steam generator might be initiated for extremely high signal levels, but the threshold is usually set so high that a rupture disk burst is likely to occur first.

The sodium-water reaction produces a broadband signal, with maximum power and amplitudes in the acoustic range (up to 20 kHz), and signals detectable at ultrasonic frequencies (80 to 500 kHz). The background noise has similar characteristics, peaking in the audio range and falling off in power and amplitude as $f^n$ (n having values of $-2$ to $-3$, and increasing with frequency). Past acoustic leak detection programs demonstrated the capacity to both detect and locate noise sources, and to detect signals totally masked by background noise. Past ultrasonic leak detection programs relied upon a positive signal-to-noise ratio being present in the chosen detection frequency band.

SUMMARY OF THE INVENTION

The present invention is an acoustic leak detection system designed for use with an LMFBR having a steam generator with an auxiliary cooling system. The vessel of such a steam generator has a large diameter which impacts the sensitivity of both chemical and acoustic leak detection systems. The sensitivity of the detection systems decreases as the diameter of the steam generator increases.

Chemical leak detection systems respond to change in reaction product (i.e., hydrogen) concentration in sodium. Since the vessel volume increases as the product of the vessel diameter squared and the vessel height, the sensitivity of chemical leak detection systems decreases as diameter increases. Thus, chemical detection systems provide inadequate protection against water leaks in large steam generators.

In contrast, the acoustic system sensitivity decreases far less as the vessel diameter increases, since the signal intensity is inversely proportional to the diameter. A further factor must be considered for the acoustic system: the steam generator operating mode. The signal-to-background noise ratio is the critical parameter, not the amplitude of the signal at the vessel wall. The acoustic system may be more sensitive if operating conditions in the larger vessel result in lower background noise levels (e.g., due to lower steam velocity).

A leak detection system does not monitor a static situation. Damage propagation results from the sodium-water reaction products impinging onto adjacent tubes and this can lead to catastrophic failure of many tubes. The initial incident must be detected and corrective action must be taken within a few tens of seconds in order to limit damage propagation. A fast and reliable acoustic leak detection system is needed since with rapidly escalating leaks, rupture disks cannot prevent serious damage to internal vessel structures. Such a system can initiate power runback and reduce steam pressure, and place the steam generator in a stable, non-escalating damage condition prior to rupture disk activation, thereby reducing costly downtime.

Chemical (hydrogen and oxygen) concentration monitoring systems are the reference leak detection system in many plants. Although they can be quite sensitive in small loops, slow response, low reliability and erratic output signals reduce their viability for large loops. This has led to the development of acoustic leak detection systems. Both low-frequency and high-frequency acoustic leak detection systems have been developed under programs of the U.S. Department of Energy. Each of these systems used signal amplitude as a discriminator.

The integrated acoustic leak detection system (IALDS) of the present invention integrates in a unique way the advantages of the low- and high-frequency acoustic systems with information from the chemical systems and plant operating parameters to provide a highly reliable and robust leak detection system. The IALDS uses a detection algorithm that rejects sources outside the vessel and uses the frequency content of the signal as a discriminator rather than an amplitude.

A general outline of the IALDS in accordance with the invention is shown in FIG. 3. The IALDS includes a sensor system and a signal processing system. The sensor system includes acoustic sensors (e.g., accelerometers) coupled to the vessel wall of the steam generator and chemical system sensors placed inside the vessel to monitor the hydrogen content of the liquid sodium and the cover gas. The signal processing system basically comprises a neural network-based preprocessor for rapid leak detection, then a beamformer-based main processor for accurate and reliable leak confirmation. The signal processing subsystem operates at three different levels of detection.

At the top level of detection a trained neural network system monitors the vessel length for any indication of a leak. The proposed approach uses discriminators which do not require any beamforming of the sensor signals. The objective of this level of detection is two-fold: (1) to indicate that a leak may be present in the vessel; and (2) to isolate the most probable part of the steam generator containing the leak.

The presence of a leak and the general location in the vessel will be decided using a fuzzy logic expert system. The decision will be based on the output from a neural network monitoring low-frequency discriminators, the output from a neural network monitoring high-frequency discriminators, and the signals from chemical monitors. The fuzzy logic system will take into account any parameters which might impact the output from the monitors, such as a recent injection of hydrazine into the feedwater.

This level of detection will provide many possible leak indications during each day, but they will not pass outside the detection system. The leak indications will be passed to a second level of detection, a beamformed system which will monitor the indicated portion of the vessel. The beamformed system will use conventional beamforming techniques. The beamformer's sensors will be selected by the fuzzy logic leak detection controller. It will tag those locations most likely to have a leak.

A third level of detection will now systematically monitor the tagged locations to determine if a leak is really present, remaining on the specific locations to detect a leak above the defined threshold to an accuracy of about one false alarm in 30 years of operation. The actions to be taken will be controlled by a second fuzzy logic expert interface controller. This will provide a rational response to the leak indication.

The IALDS will provide a human computing machine response to the leak indication. For example, instead of initiating an automatic shutdown, a controlled reduction in power can be started. If this reduces the temperature in the vessel, the damage propagation rate is reduced, and the fuzzy logic interface controller can make the appropriate change to the shutdown. As the system is moved towards shutdown, the background noise will reduce, with commensurate increase in detection capability. Again the interface controller will take account of the change. It is possible the response will be a return to power if the signal is not confirmed at the lower power level. Alternatively, if rapid escalation occurs, the interface controller will respond with a faster shutdown or, if appropriate, vessel blowdown to minimize damage to the overall intermediate heat transport system. The interface controller will provide a more human judgment response characteristic than previous systems were capable of providing.

BRIEF DESCRIPTION OF THE DRAWINGS

FIGS. 6A and 6B are schematics of the respective transducer (accelerometer) amplifier subsystems in accordance with first and second preferred embodiments of the invention.

DETAILED DESCRIPTION OF THE PREFERRED EMBODIMENTS

Figure 1:
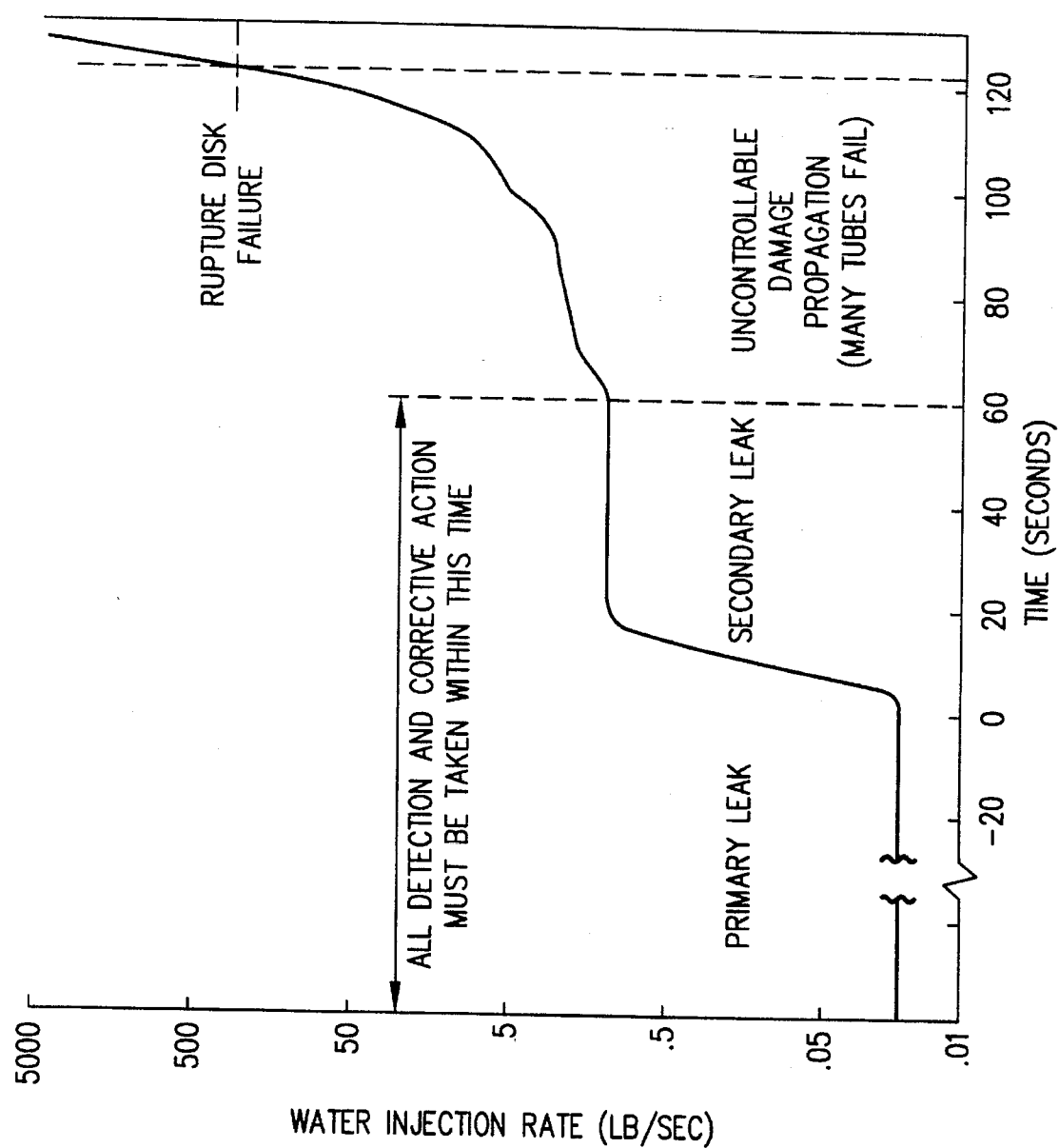
FIG. 1 is a graph showing the escalation of the water injection rate over time for leakage of water into sodium in a steam generator.

Acoustic pressure fluctuations from a sodium-water reaction impinge on the vessel wall of the steam generator, causing the wall to displace. In the acoustic detection system of the invention, this local wall motion is monitored by externally mounted transducers.

If spatially unique assessments of the arrival times of such fluctuations are required, each part of the wall must move independently. One of the prime requirements for a low-frequency acoustic detection system is to choose a frequency range in which the wall movement is inertia (or mass) controlled, not stiffness controlled. The wall will then respond at any point with an acceleration proportional to the force exerted on the wall at that point. A preliminary assessment indicated inertia-controlled frequency limits of 1 to 13 kHz for the steam generator shell.

Experimental evidence indicates sodium-water reactions produce random noise having a bandwidth of about 10 kHz. There is no evidence that any characteristic frequencies are generated. Therefore, all analysis of data is based on the following assumptions: (a) The sodium-water reaction is a randomly excited acoustic pressure source having a Gaussian distribution of variables in the frequency band 1 to 13 kHz; (b) An ambient pressure level is randomly generated in the volume of the vessel with a Gaussian distribution of noise generation sources in the frequency band 1 to 13 kHz.

The signal-to-noise ratio is defined as the acoustic intensity at the wall due to direct acoustic pressure waves generated by the sodium-water reaction, compared to the acoustic intensity from all other sources in the vessel concurrently reaching the sensor location. (This includes any waves from the sodium-water reaction which have experienced reflections prior to reaching the wall, i.e., reverberation energy.) The background noise amplitude at the wall of the steam generator is the resultant of several acoustic generating sources: noise generated by flow of sodium through the vessel; noise generated by the flow of steam or water inside the tube bundle; noise generated by the boiling of water inside the tubes; electronic noise associated with the acoustic monitoring system; farfield noise transmitted into the steam generator; and reverberation energy due to the leak source. To predict IALDS performance, the amplitude of each of these components must be predicted as a function of operating conditions.

A carefully designed and executed program measured the absolute amplitude of the noise from a sodium-water reaction. Reverberation characteristics were measured first using several independent techniques. Knowing the reverberation characteristics allowed the measured signals to be separated into direct and indirect components. A wide range of test conditions, including injection rates up to 10 gm H$_2$O/sec, allowed a general correlation to be obtained for sodium-water reaction noise at 30 cm from the source:

$$A=200G^{0.5}$$

where A is the absolute signal amplitude (μbar); and G is the water injection rate (gm H$_2$O/sec). Test data indicated this equation is also valid for predicting noise levels from intermediate leak sodium-water reactions. The actual signal power reaching the sensors will depend upon the distance d of the sensor from the source. The vessel can be considered acoustically homogenous, producing spherical dispersion of acoustic energy away from the source location, so the signal intensity at the sensor is inversely proportional to d.

The acoustic detection/location system of the invention has a maximum efficiency when the beamformer resolution grid matches the signal source width. The source width is defined by assuming two sources exist at the same location, and then moving one of the sources away until it has a separate identity. This is equivalent to taking the autocorrelation of the noise, then defining that spatial resolution between two close sources would occur at the point of inflection of the autocorrelation. The point of inflection is equal to g/2, where g is the wavelength at maximum frequency of selected noise bandwidth. Typically a sodium-water reaction has an autocorrelation bandwidth of 10 kHz, which means the spatial resolution of the acoustic detection/location system is about 12 cm in sodium. Sources closer than 12 cm may not be differentiated, i.e., if two close sources (<12 cm) are present in the vessel, the IALDS will indicate a stronger noise (integrated power) source for the nodal point.

In searching the steam generator volume for a noise source, it is sufficient therefore to assume that the steam generator consists of a three-dimensional array of 12-cm cubical elements. Each cubical node is sequentially scanned by the acoustic detection system and the absolute noise generation at the location is measured. The length of the ALMR steam generator results in about 200 planes in the doughnut-shaped space between the inner duct and the outer flow shroud. Each plane contains about 1200 array focus points (volume elements) in the helical coil region due to the large vessel diameter.

A simplified interpretation of the effect of using an array of sensors is to consider an array as a signal amplification device. Two parameters effect the array gain: (1) sensor density per unit axial length of the vessel; and (2) location of the leak in the measurement plane.

Increasing the number of sensors located on the measurement plane increases the array gain. For a given number of sensors the array gain is also a function of their density per unit length of the vessel. As the sensors are moved away from the plane, the distance between the sensor and the leak source increases, resulting in a reduced signal level compared to that measured on the same plane as the source.

The second parameter which affects the array gain is the location of the leak source. The leak moves closer to some of the sensors and away from others as the leak is moved away from the central position in the plane, resulting in a decrease in the array gain. It should be noted the array gain is not a function of the intensity of the noise source. Array gain is defined as a ratio, with the reference as the signal intensity from a central source measured at a location on the periphery of the measurement plane. Changing the diameter of the measurement plane will affect both the reference and array intensities equally, and give a constant array gain. A major impact on signal-to-noise ratio will result as the measurement diameter plane is increased. The background noise intensity remains constant, but for a constant leak source the measured signal intensity at the vessel wall is inversely proportional to the diameter. Increasing the array gain by increasing the sensor density will result in an improvement in signal-to-noise ratio for a constant diameter.

A computer program can be used to aid in setting the sensor density and location geometry. The array design criteria will include: (1) the geometry of the steam generator; (2) an array gain which is nearly constant at any leak location in the measurement plane; (3) a signal-to-noise ratio of −25 dB for a leak rate of 0.1 gm H$_2$O/sec at any location in the measurement plane; (4) a false alarm rate of one in 30 years per steam generator unit; and (5) an optimized sensor density and optimized geometry for simple sensor attachment to vessel. The two controlling parameters are the minimum leak rate and detection in a given time. The second parameter (detection time) is directly calculated from signal-to-noise ratio and false alarm rate. The signal-to-noise ratio depends directly upon the array gain, which is a function of sensor density. The size of the leak to be detected and the maximum time allowed for detection control the number of sensors needed. In accordance with the preferred array, sensors were located axially on a three start helical pattern, with eight sensors per meter of vessel axial length.

The main components of background noise in a steam generator at the sensor location can be classified as nearfield or farfield noise. Nearfield noise is a direct pressure fluctuation onto the vessel wall at the transducer location from a nearby noise source. Far-field noise propagates inside the vessel as acoustic pressure waves, and has reverberant properties due to the potential for multiple reflections before the wave impinges onto the vessel wall. Two properties of nearfield and farfield noise are of importance to acoustic leak detection: the degree of spatial coherence from any background noise source at each location of sensors in an array; and the magnitude of the noise at the location of individual sensors mounted on the steam generator vessel wall due to all possible background noise generators.

The spatial coherence of a noise generator, such as a leak, is used as the main sodium-water reaction detection index. Any other strong, localized source within a vessel could confuse leak detection. Analytical estimates confirmed by measurements in steam generators have shown background noise generation does not have strong nearfield spatial coherence. The main source of nearfield noise is sodium flow since this is in contact with the wall. Flow noise is coherent only over distances similar to the magnitude of eddy sizes; and typical eddy dimensions are much smaller than the separation between sensors in an array. When the farfield noise is the result of a distributed network of noise sources, as from boiling within tubes or a number of orifices in a flow distribution plate, the large number of reflections will tend to produce a generalized incoherent increase in background noise at sensors in an array. Test results confirmed that very low levels of spatial coherence are present in the background noise of a helical coil steam generator.

The second parameter is the magnitude of background noise at each sensor location. The background noise amplitude will vary depending upon the axial location along the vessel. Under operating conditions producing intense turbulent flow, nearfield noise will be the dominant background noise source at each location. It was predicted and confirmed that turbulence noise was proportional to the fluid velocity to the cubic power.

When the steam generator is at hot standby or low part load conditions, the reverberation noise from sodium-water reaction/leak generated noise can became the main source of background noise. Farfield reverberant noise from an intermediate or large leak will dominate as the background noise under these steam generator operating conditions. The overall magnitude of the farfield noise is low for small leaks, and in some instances is composed primarily of electronic noise associated with the transducer and electronic hardware. Data indicated reverberation noise will be about two times the direct noise from the leak site.

Since the sound produced by steam flow is a cubic relationship, it is expected that the background noise will fall significantly as the power is reduced. This reduction increases detection sensitivity. For example, if the power reduction and steam velocity are directly proportional, the noise at 80% power would be 51% of the full power noise; or about 405 µbar, compared to the full power noise amplitude of 790 µbar. A similar reduction will apply for the amplitude of the noise generated as water flows through the gagging orifices in the water inlet tube sheet region.

The transmission of energy from the source in a steam generator to the detector on the vessel wall follows two paths. The first path is through the sodium; the second through any contiguous metal structures. Ultrasonic energy traveling radially through the sodium will be attenuated. An experimental correlation was derived for the attenuation factor for propagation through sodium in the 180 kHz band:

$$\text{Attenuation in Na} = 0.214 \times 10^9 \times d^{-0.667} T^{-3}$$

where d is the distance between the noise source and the transducer (inches); T is the average temperature between the source and transducer (° F.). Typically about 5% of the original energy is measured at a distance of 100 inches through sodium at 600° F.

The following conclusions were drawn from the experimental data: (1) signal intensity is highest at a frequency governed by the leak orifice geometry, and falls significantly as the monitored frequency increases or decreases; (2) signal loss (attenuation) increases as the monitored frequency increases; (3) signal loss (attenuation) due to impedance mismatch and convoluted metal path between the source and sensor is more significant than signal attenuation along a tube; and (4) signal transmission through the sodium is the most likely mode of ultrasonic energy transmission to the sensor.

Two main classes of ultrasonic background noise sources exist: those due to normal operation of the steam generator, and farfield noise and noise generated during transient operation of the steam generator. The following parameters were found to be sources of background noise during laboratory and steam generator operation monitoring: (1) water flow noise; (2) steam flow noise; (3) water boiling noise; and (4) sodium flow noise.

The IALDS in accordance with the invention uses externally mounted accelerometers to monitor the acoustic pressures within the steam generator vessel by measuring the resultant wall motions. Externally mounted accelerometers are preferable to internal microphones for the following reasons: accelerometers are accessible during operation; accelerometers can be replaced without penetrating the water or sodium circuits; accelerometers are solid-state devices, i.e., they are robust and expected to have long operating lifetimes; accelerometers are much lower in cost than are high-temperature microphones.

High-temperature (475° C.) accelerometers are extremely expensive, and their performance and reliability uncertain. In accordance with the invention, a thermal stand-off allows low-temperature accelerometers (250° C.) to be used on the steam generator. A "stripped-down" version of commercially available accelerometers can be used for the IALDS, with an integral hard-wired cable replacing the usual connector.

Figure 3:
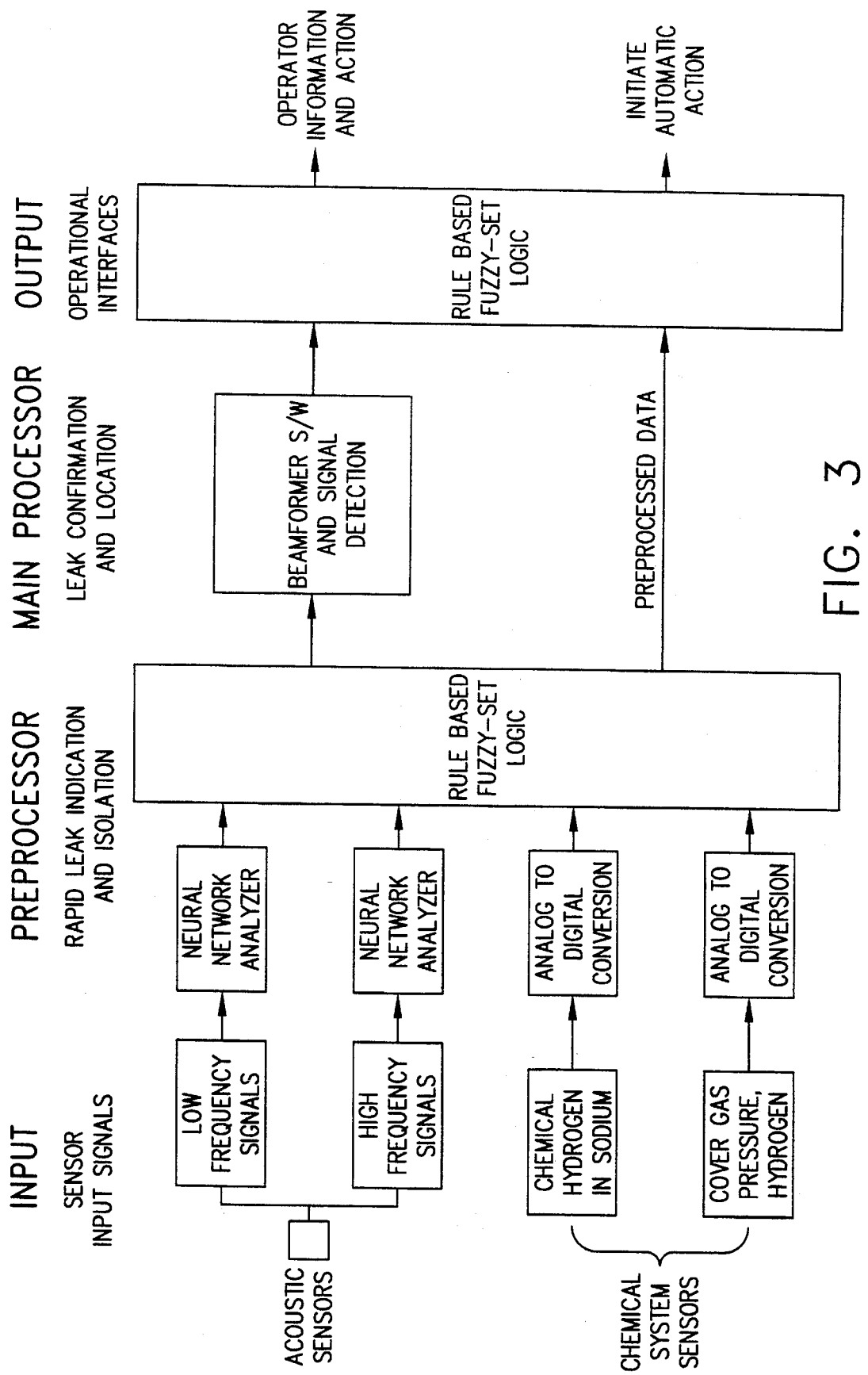
FIG. 3 is a block diagram of the integrated acoustic leak detection system in accordance with the invention.
Figure 3A:
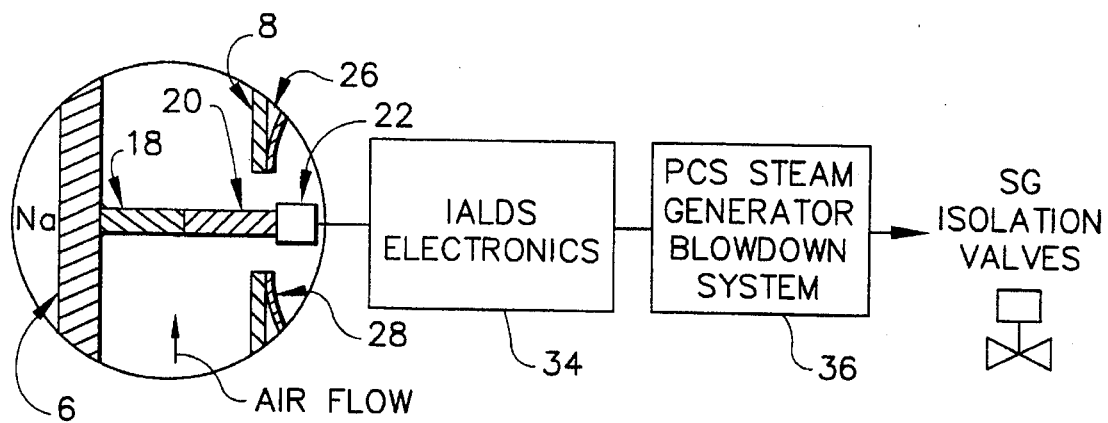
FIG. 3A is a schematic of the integrated acoustic leak detection system in accordance with the invention, showing in detail the sensor mounting on the steam generator vessel of FIG. 2.
Figure 4:
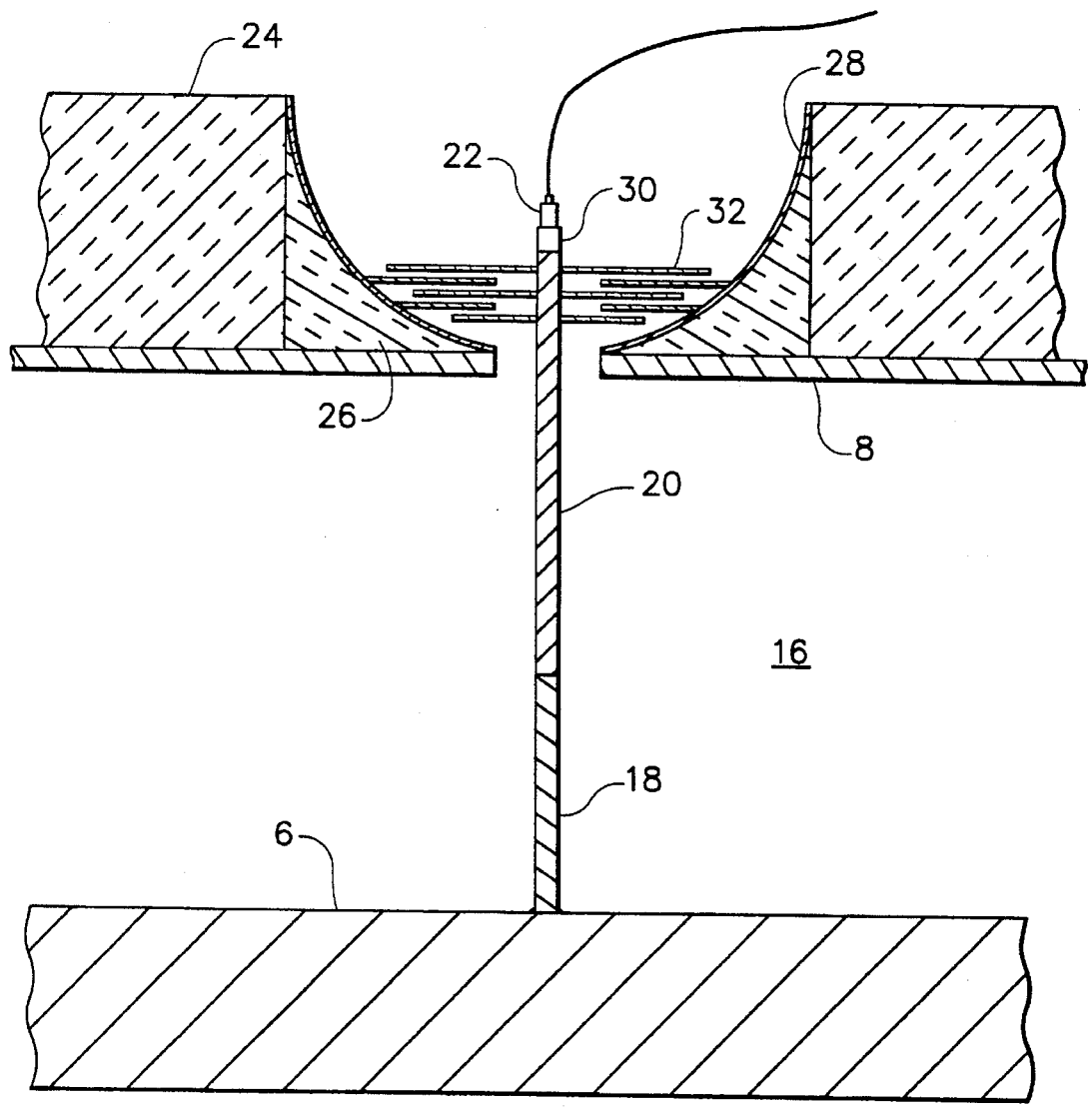
FIG. 4 is a sectional view of a transducer (accelerometer) subassembly in accordance with one preferred embodiment of the invention.

A problem specific to the current design of the ALMR steam generator is attachment of the transducers to the steam generator shell. Referring to FIG. 4, an auxiliary cooling system (ACS) duct 16 surrounds the shell, and the accelerometer must be attached to the shell through this duct. The annulus between the duct and steam generator is expected to be at a similar temperature to the steam generator shell, and far in excess of the maximum allowable accelerometer temperature. A conceptual design of the accelerometer mounting scheme is shown in FIGS. 3A and 4. The low-frequency system requires the accelerometer to monitor the motion of the steam generator shell. The mass of the accelerometer increases the effective mass of the wall, but has only a second-order effect on signal amplitude. The high-frequency system monitors the transmission of ultrasound along the attachment rod.

An accelerometer mounting is shown in FIG. 4. A steel stub 18 is attached to the vessel wall 6. A metal alloy extension 20 allows the transducer (typically an accelerometer) 22 to be placed outside the shroud 8. The steel and alloy rods 18 and 20 have a diameter in the range of ⅛ to ¼ inch and act as a waveguide for ultrasonic waves. Normal heat insulation 24 is used on the shroud, and high-efficiency thermal insulation 26 is packed into the immediate region of the accelerometer as shown. The insulation is held in place with a light metal cup 28, made in the form of a clamshell for convenience in assembly. The clamshell is attached to the outer shroud. Thermal protection and thermal isolation of the accelerometer 22 is provided by the foamed glass insert 30 mounted between the accelerometer 22 and the alloy stub 20. A labyrinth seal assembly 32 may optionally be attached to the alloy stub 20 and cup 28 to reduce the flow of hot air from within shroud 8 and prevent overheating of accelerometer 22.

Figure 2:
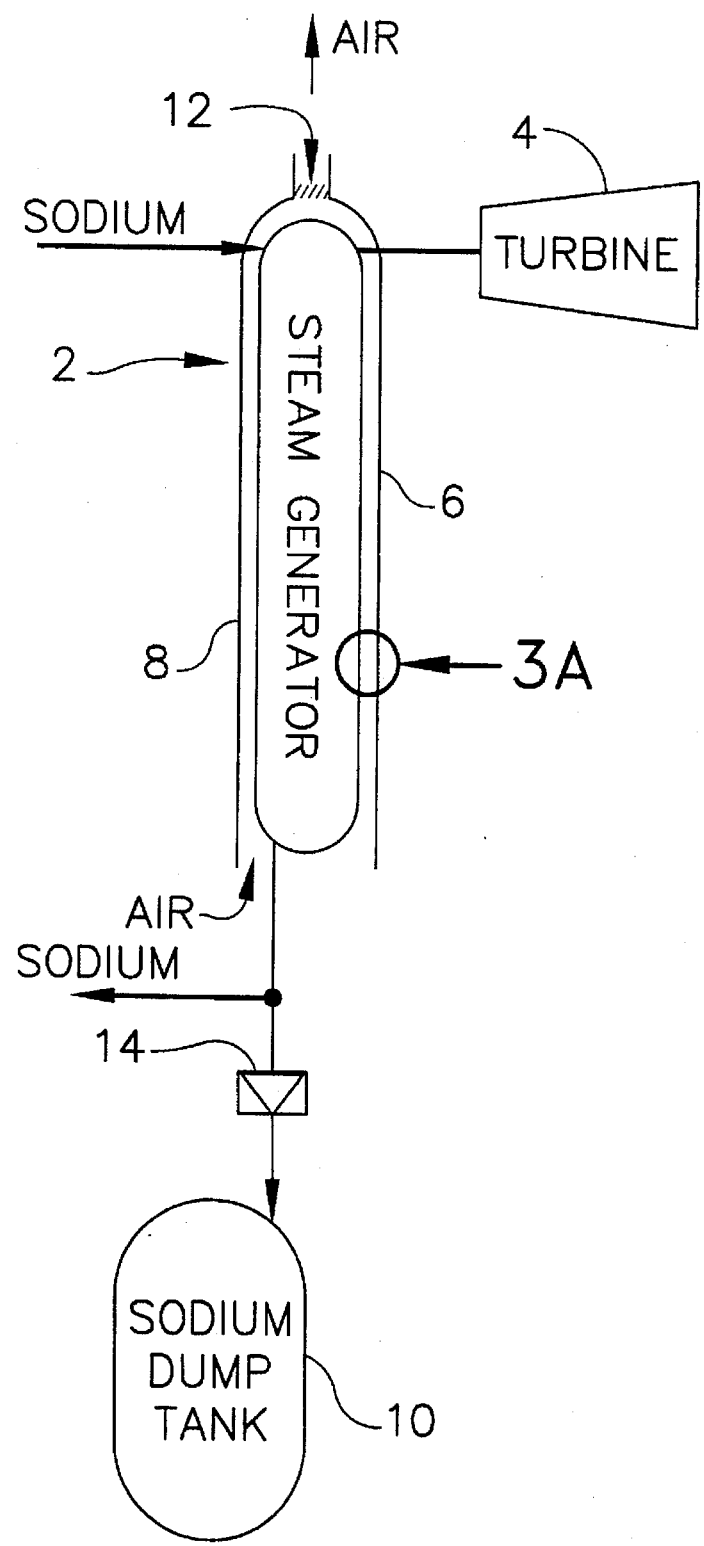
FIG. 2 is a schematic of the secondary heat transfer system of a liquid metal fast breeder reactor showing the location of a transducer in accordance with the invention.

The location of the transducer (accelerometer) subassembly is shown in FIG. 2. A multiplicity of transducer assemblies are attached to the steam generator vessel outer wall 6. Each accelerometer sends an analog electrical signal to the IALDS electronics 34, which control the steam generator blowdown system 36 (see FIG. 3A). The output of the blowdown system 36 activates the steam generator (SG) isolation valves.

Figure 4A:
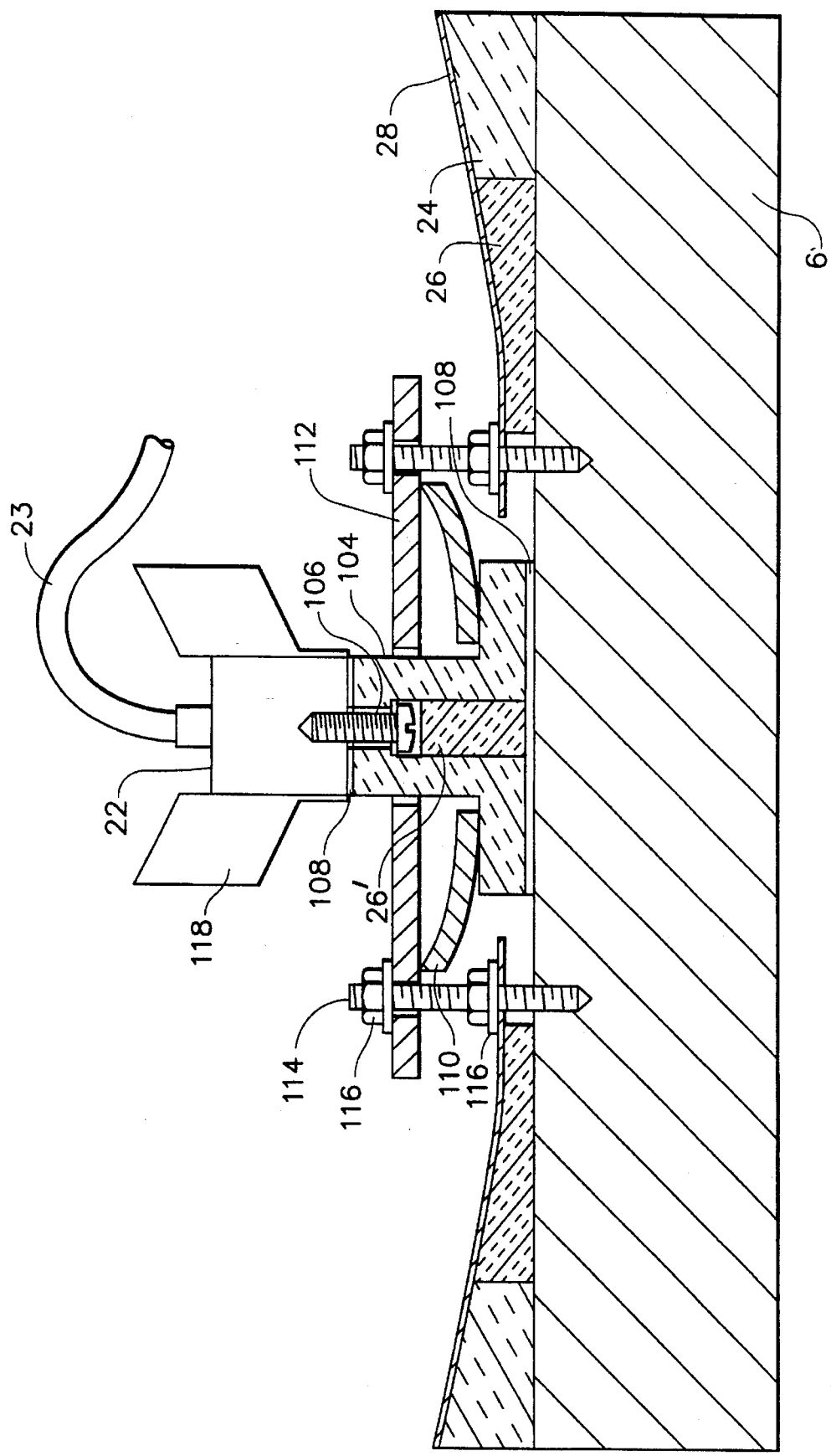
FIG. 4A is a sectional view of the transducer (accelerometer) subassembly in accordance with another preferred embodiment of the invention.

Alternatively, for steam generators not constructed with an outer shroud, the accelerometers can be mounted directly on the vessel wall with suitable thermal insulation to isolate the accelerometers from the heat emanating therefrom. In particular, the accelerometer 22 can be coupled to vessel wall 6 by a ceramic thermal insulator standoff 104 (without a steel/alloy attachment rod), as shown in FIG. 4A. This subsystem further comprises the following components:

accelerometer cable 23; normal insulation 24; high-efficiency insulation 26, 26'; metal cup insulation holder 28; accelerometer holding screw and washer 106; acoustic couplant 108; Belleville spring washer 110; hold-down plate 112; threaded post 114; nut and washer 116; and thermal radiator 118.

Figure 5:
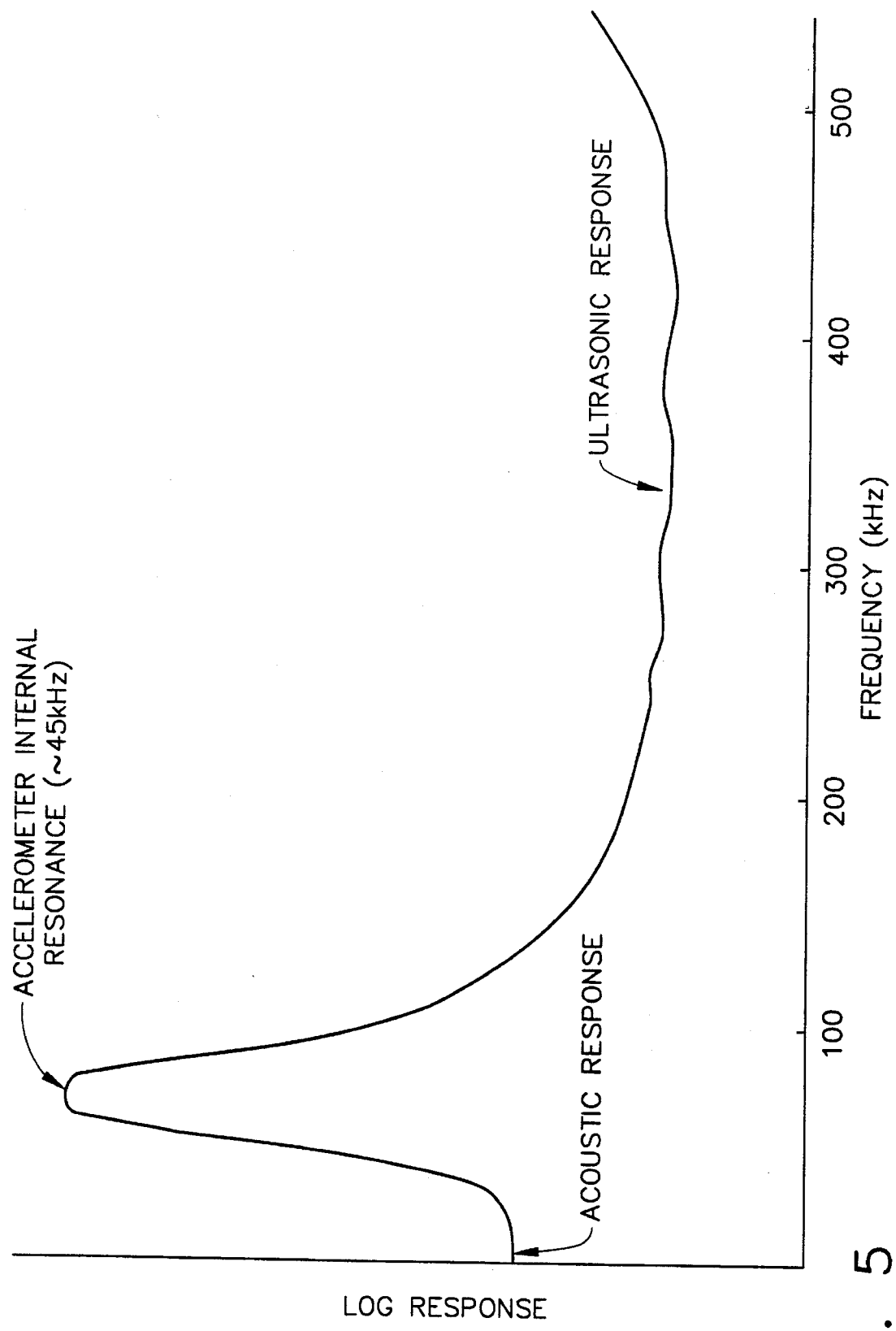
FIG. 5 is a graph showing the response characteristic of an accelerometer.

A typical response characteristic of the transducer assembly to high- and low-frequency acoustic noise is shown in FIG. 5. The low-frequency acoustic response is typically in the range of 100 Hz to 15 kHz. The internal transducer resonance is in the region of 45 kHz. The effective high-frequency ultrasonic response ranges from about 80 kHz to several hundred kilohertz.

Significant savings as well as an increase in reliability and reduced maintenance requirements result from monitoring low- and high-frequency signals using a single transducer. Transducers are designed to provide a flat response over the low-frequency bandwidth (approximately 10 Hz to 15 kHz). This is achieved by designing the mechanical structure holding the piezoelectric crystal 38 (see FIGS. 6A and 6B) to resonate at about three times the highest frequency in the specified bandwidth. For the transducer response of FIG. 5 this would be a resonance at about 45 kHz. Between 15 and 45 kHz the response becomes increasingly nonlinear and falls off systematically above the resonant frequency. The low-frequency response is a function of the electrical characteristics of the crystal. Similarly, a high-frequency transducer has a linear response from about twice the resonant frequency to an upper limit. The upper limit is a function of the stray electrical characteristics of the crystal, but is usually in the range of about 500 kHz. The upper linear response is about 100 to 500 kHz, but with a much lower signal amplitude than the low-frequency region.

A first design for the sensor electronics (see FIG. 6A) uses a high-temperature broadband amplifier having a large dynamic range, e.g., gallium arsenate amplifiers. The signal conditioning subsystem for the first concept comprises a powered high-temperature preamplifier having two stages: a low-gain amplifier 40 followed by a high-gain (logarithmic) amplifier 42, internal to accelerometer 22a. The preamplifier 40 is powered from an external power supply 54 through a cable subassembly 50. The cable has a dual function of also carrying the outgoing high- and low-frequency accelerometer signals to the signal conditioner 52.

The second design is a dual-frequency version having a high-frequency, band-limited amplifier 48 which splits off the high-frequency signal close to the transducer 38 using a high pass filter 44. The low-frequency signal is transmitted via a passive low pass filter 46 to the low-frequency portion of the signal conditioning subsystem 52.

The IALDS sensor subsystem in accordance with the invention is based on low-cost, robust and reliable, commercially available components for detection of both low- and high-frequency signals; has approximately the same number of transducers monitoring for low- and high-frequency signals; produces stable signals for subsequent analysis and reliable detection of a leak; and allows discrimination between leak signals and plant-originated signals.

The sensor subsystem comprises vibration sensors capable of simultaneously operating over multiple independent frequency ranges. The sensor subsystem incorporates frequency separation within the sensors, amplification of the higher-frequency components and transmission of each component on its own conductor or mixing of the two components with transmission along a single central conductor, shielded cable.

The sensor mounting structure enables the sensor to detect mass-controlled motion of a steam generator wall simultaneously with the independent detection of the higher-frequency-controlled ultrasound vibration energy transmitted along the attachment rod (18, 20 in FIG. 4). The sensor mounting structure limits the amount of heat energy conducted to the acoustic vibration sensor without active cooling such that common, inexpensive piezoelectric/piezoresistive semiconductor materials and sensor designs may be employed. This thermal stand-off allows the use of low-temperature (<250° C.) acoustic vibration sensors on a high-temperature (typically >475° C.) steam generator vessel. Further, the foamed glass inserted in the signal path prevents heat conduction to the sensor while passing the vibrations to be detected. This sensor mounting structure permits both easy steam generator/auxiliary cooling system shroud assembly and easy acoustic vibration sensor installation or, if necessary, replacement (while the steam generator is in full operation).

In addition, the sensor mounting structure includes a welded steel stub for sensor attachment to the wall of the steam generator vessel. The weld impacts a volume of the wall material that is less than the defect volume recommended by ASME for material structural failure analysis. Thus the sensor attachment does not decrease the safety performance of a steam generator vessel wall.

The number of sensors placed onto the vessel is a compromise between shorter detection times and cost for a given size of leak. The performance of an array of sensors is primarily a function of the surface density of accelerometers on the vessel. The second factor governing the number and location of accelerometers on the steam generator shell is signal attenuation. The amplitude of any pressure wave leaving the leak site will decay as it spreads out from its source. The intensity of the signal will fall in direct relationship to the distance between the signal source and the sensor location. It should not be assumed that the signal level falling will reduce the signal-to-noise ratio for a given leak size. If the water/steam velocity and the sodium velocity are lower in the larger vessel than in a smaller-diameter vessel, the background noise may be significantly lower. The signal-to-noise ratio may tend to remain constant as the vessel size increases. The background noise is proportional to the velocity cubed. A reduction in the steam flow velocity from 100% to 80% is equivalent to a reduction in background noise to 50% of the background at 100% velocity. The signal noise amplitude can be reduced by a similar amount, equivalent to a vessel diameter increase of about 25% for the same signal-to-noise ratio. As the vessel increases in diameter, the number of focal points increases almost as the ratio of the square of the vessel diameter. This means the number of calculations needed also increases by the same factor. This increased computational load can result in an increased number of digital signal processing units to enable all calculations to be completed in the specified detection time.

The analog processing subsystem is a module which can typically handle 32 inputs from the transducers. The signals from the transducers are taken to individual sample and hold (S/H) chips for almost simultaneous capture. The high impedance of the S/H allows the accelerometers to be connected directly to the S/H input. A single high-speed analog-to-digital (A/D) converter transforms the S/H voltages to digital values. These are then loaded into a true first-in first-out (FIFO) buffer. The full FIFO buffer of data is then transferred under the control of the host computer to one or more (typically three) analysis units. A parallel FIFO buffer is now filled with new data as the first FIFO buffer data is transferred out. Data arrays are transferred via a switch in alternating fashion from the two FIFO buffers to provide real-time data capture.

Data are collected in the FIFO buffer, which typically holds 64 KB of 16-bit words. An interface between the data acquisition module and a host computer provides direct memory access transfer from the FIFO buffer. New data are always available when requested by the processor, allowing real-time data monitoring. An RS232/485 type serial (or parallel) port is provided, possibly attached to a local microprocessor, to provide "Smart Access" to the data for ancillary diagnostic functions, or for local monitoring of data by a technician or operator.

The data from each transducer (typically an accelerometer) are normalized. The root of the mean squares of all the data captured from the individual transducer (or a separate dedicated chip providing a similar signal average power) is the scaling/normalization factor. This automatically compensates for differences in calibration factors of the sensors.

The IALDS further includes a three-dimensional sound/noise field monitoring algorithm which is optimized for leak detection. The algorithm provides a full three-dimensional mapping of the noise field, and accommodates the zoom capability (described below). The data array can be analyzed using either time or frequency domain versions of the mapping algorithm. The output of the mapping beamformer is due to the addition of the source power at the array focal point and the local background noise at each sensor location. The diagonal terms of the array covariance matrix corresponds to the auto-covariance of each sensor signal and contains no signal source information. The off-diagonal terms contain information of both the signal source-to-sensor attenuation and the source's location. The algorithm extracts this source information, and converts it to a direct measure of the absolute noise intensity at each possible location (array nodal point) in the monitored field.

These outputs of the sensors are monitored by neural networks to extract the presence of a leak from the background: one network for high-frequency monitoring and the other for low-frequency monitoring. The neural networks will use both the raw signal and signals processed to improve leak discrimination (such as the power spectral density of the sensor signals). The neural networks effectively perform pattern recognition on the signals input in parallel thereto. If there is any indication of a leak, the inputs to the neural network will be examined to assess those sensors most likely to be the leak indicators.

The importance index is an algorithm developed to identify which inputs are strong discriminators in predicting the output of the neural network preprocessor, or of a fuzzy logic preprocessor. The trained neural network connection weight matrix between input, hidden layers and output will be processed to provide an "importance index" for each input (an input is generally a preconditioned sensor signal). This algorithm measures or partitions the ability of each input to cause a specific neural network output by calculating the relative impact of each input compared to all other inputs. For example, although the neural net may have over 100 inputs, not all will affect the output. The partitioning algorithm allows extraneous inputs to be identified and considered for removal. The fuzzy logic preprocessor will then adjust the testing tolerance to see if the leak is also indicated by the other neural network monitor but at a lesser degree, and will also assess any change in response of the chemical monitor(s) and process parameters. If a leak is suspected, the fuzzy logic expert preprocessor will then use an importance index to decide which section of the vessel is most likely to have a leak. The importance index for the fuzzy logic preprocessor is embedded in the rulebase. The output of the neural net preprocessors and input from other sensing systems, such as the chemical detection subsystem, are partitioned according to a partitioning algorithm defining the input's relative importance. The output of eight sensors monitoring the section identified will then be beamformed to locate the leak using the low-frequency beamformer technology described below.

The outcome is passed to the fuzzy logic processors. The second fuzzy logic expert system will also examine the high-frequency signal from the same sensors chosen for the low-frequency location analysis, and concurrently assess the response of chemical monitor(s) and process parameters. If a leak is detected, the processor assesses leak size, false alarm rates and initiates the correct action appropriate to the predicted size of the leak and reliability of detection. This can be a decision to reduce steam generator operating power and increase detection reliability, or to shut the steam generator system down. If the decision is to reduce power, the processor sends instructions to the preprocessor on how to continue monitoring for a leak, such as changing testing tolerance or extending analysis time for the beamformer system analysis.

Figure 7:
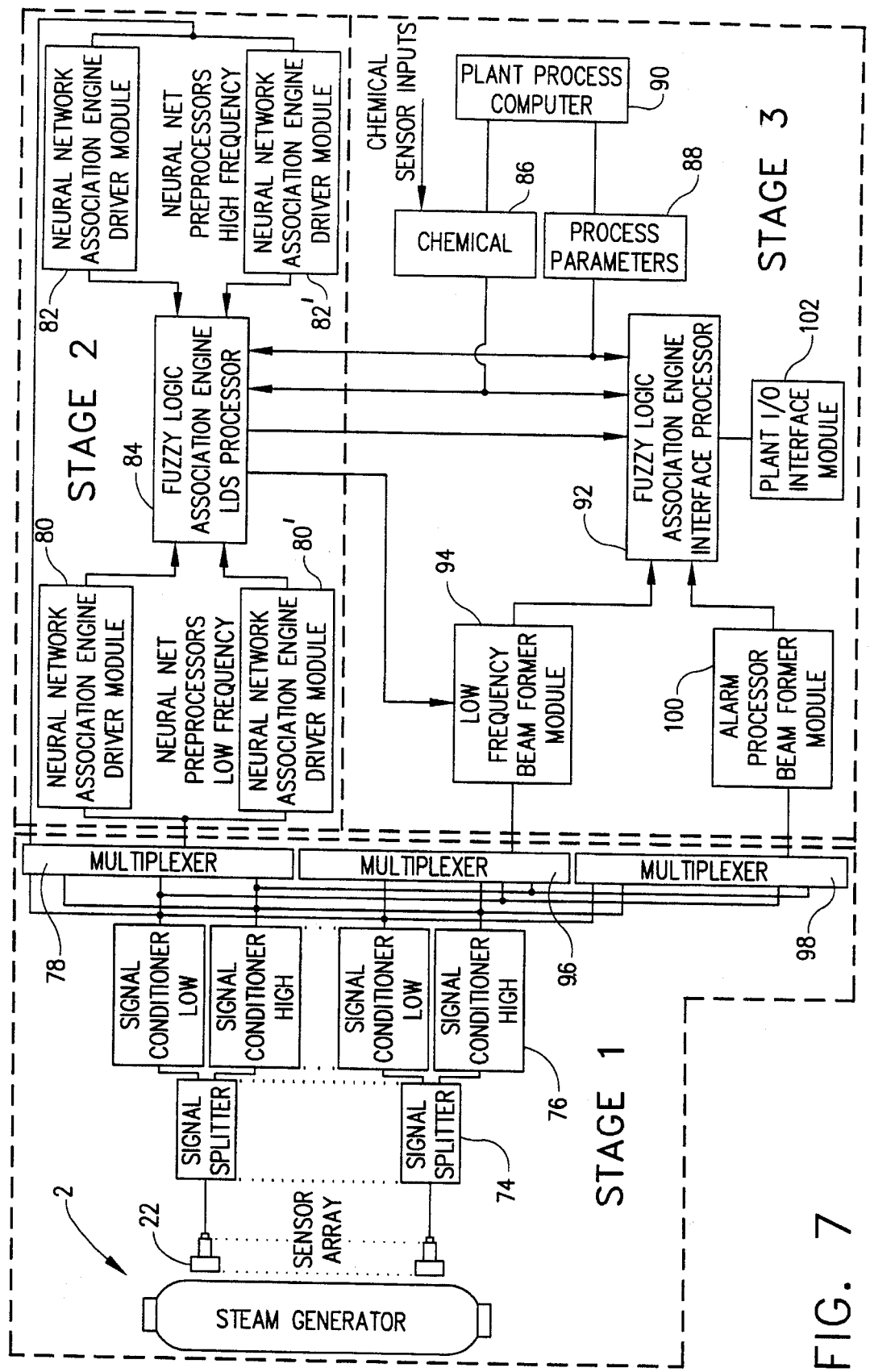
FIG. 7 is a block diagram of the steam generator leak signal processing system in accordance with the invention.

A diagram of the system is shown as FIG. 7. All of the acoustic sensors 22 have their output signal split into high- and low-frequency signal components by signal splitters 74. The low-frequency signals are transmitted along cables to a signal conditioning module 76. This module contains all amplification and bandpass filter components. The signal conditioning module transfers the signals to three parallel connected and independently controlled modules. The first module has a multiplexer 78 which transfers all low-frequency signals to the neural network association engine-driven preprocessor system 80, 80' for analysis. A similar set of modules 82, 82' performs the same functions on the high-frequency signals. The fuzzy logic association engine-driven module 84 has inputs from the low- and high-frequency preprocessor neural network modules, inputs from the chemical monitors 86 and process parameters 88 received from the plant process computer 90. If the fuzzy logic association engine 84, after analyzing this input, decides a leak is present in the vessel, it provides information on the probable axial vessel location to the fuzzy logic interface processor 92, and to the low-frequency beamformer module 94. The latter module selects the optimized array of sensors to examine an axial section using the second multiplexer 96. An analysis is made by the beamformer module 94. The output of this analysis is passed back to the interface processor 92. If the interface processor requires further detailed analysis to provide greater reliability (low false alarm rate), it uses the third multiplexer 98 to select the appropriate sensors from the array 22 for leak confirmation by the alarm processor module 100. The low-frequency beamformer 94 confirms the leak indications from the high-frequency preprocessor 82, 82', the low-frequency preprocessor 80, 80', or the chemical monitors 86 of the steam generator 2. On the basis of the overall responses of the acoustic, chemical, and process parameters, the interface processor 92 transmits corrective action to the plant I/O interface module 102.

The fuzzy logic preprocessor receives crisp (or discrete) input values from each of the neural net preprocessors, process instrumentation, and acoustic and chemical leak detection systems. One traditional approach for representing a system (linear or nonlinear, time invariant or time series, etc.) is by tabulating all possible inputs to the system and the possible responses or output of the system to all combinations of inputs. This type of approach is at best crude and unwieldy, and often impractical. System designers attempt to accommodate these limitations by simplifications, which may limit the range of applicability when installed onto real-world systems. The fuzzy logic preprocessor significantly reduces the table size (or rulebase) by assigning the input points to input regions or fuzzy sets. Fuzzy sets provide interpolation between regions of constant value input. Fuzzy sets can overlap, causing multiple rules to fire when the input is in an overlapping range. This allows representation of vague, uncertain or approximate knowledge through the use of linguistic variables. This approach allows systems so complex as to be analytically intractable to be represented in words rather than numbers.

A sodium-water reaction, its location and alignment, potential for initiating damage propagation, the variation in composition and transport of reaction products, the influence of steam generator operating conditions, and the complex characteristics of the monitoring systems produce a very complex system. Each of these parameters has been examined experimentally and analytically, and information and models are available which lend themselves to classifying inputs into fuzzy sets, the overlapping of the fuzzy sets accommodating the inherent variability in defining precise relationships between input and output. Because fuzzy rulebase systems make no assumptions as to linearity, they can also be applied to nonlinear relationships. For example, leaks are often classified as microleak, small leak, intermediate leak, large leak, etc. No precise limits are definable for each class, but there is fairly general agreement on the range of leak rates (with overlap) for each class. Many of the detection characteristics are also classifiable in relation to these classes of leak. Although any single input to the fuzzy logic preprocessor could cause a specific response, interaction between the input sets provides a more reliable output response. For example, a small increase in one detection system input might not be considered sufficient evidence to take corrective action, but several detectors each producing a confirmatory small input will increase the probability that corrective action is initiated.

The input is fuzzified to provide a smooth transition between all possible crisp inputs. The system responds according to the inferences drawn from the fuzzy rulebase. The outputs from the preprocessors are defuzzified to provide very crisp or discrete responses or values. The system will generally operate in a normal operating regime. This is centered around an acceptable output which accommodates minor perturbations, noise and expected changes. The normal response would be no corrective action. The system may also infrequently enter an extended operating regime, such as startup and shutdown of the steam generator. The output must again be crisp, responding to and accommodating the larger variations in steam generator and possibly detection system operating conditions. It is possible the system will very infrequently enter an abnormal operating state. Although very infrequent, it is of equal importance to the other operating states and an appropriate crisp output must be provided to the operator. An example of an abnormal state is steam leaking to the atmosphere from a flange, or even failure of the protective rupture disk. Accounting for abnormal (or even impossible) states is part of the fuzzy logic preprocessor design and definition of crisp response outputs. One specific crisp output of the first fuzzy logic preprocessor (84) is defining the set of sensors to be used by the passive acoustic tomography beamformer system (94, 100). This system can then confirm the presence or absence of a leak to the appropriate false alarm criteria. The second fuzzy logic preprocessor (92) will apply its fuzzy logic rulebase inference engine to all of its fuzzified inputs and provide a crisp output to the operator to initiate corrective action. For a higher level of inputs, the crisp output would be to initiate a specific set of control actions automatically (102). For another set of inputs, the preprocessor may initiate a change in steam generator operating mode to increase the acoustic signal-to-noise ratio, for example, a reduction in power to reduce the background noise amplitude and increase the sensitivity and accuracy of the IALDS. The characteristics of the preprocessors have been described in terms of the steam generator. In the more general case, many other possible applications have similar multifactor, multivariate characteristics.

The processing system, in accordance with the invention, further has a variable dimension nodal mesh to provide spatial zoom capability. The size of the nodal mesh is defined as the effective size of the local noise source. This is estimated from the autocorrelation of the output from the noise source. The assumed size of the noise source is a direct function of the source bandwidth. The source bandwidth for a sodium water reaction is about 10 kHz. However, mesh size is not an absolute quantity for all potential applications. When monitoring for a noise source with a different bandwidth, or to more closely map a localized noise source, the nodal mesh must be changed. Typically a noise with a 20 kHz bandwidth would increase the number of mesh nodes by a factor of four compared to a 10 kHz bandwidth noise. An increase in the data sampling rate of a factor of four would result. The beamforming subsystem uses A/D converters which allow the clocking (sampling) frequency to be easily changed. At the same time filters before the S/H and A/D circuits automatically track the changed conditions.

Figure 8A:
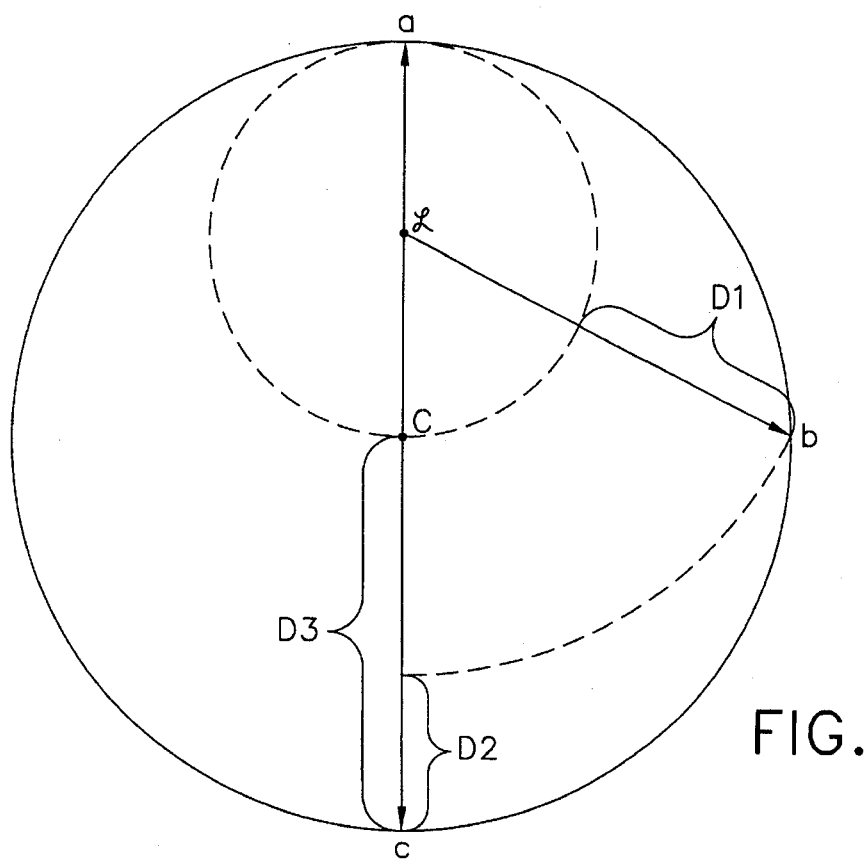
FIGS. 8A and 8B are diagrams showing the basic concept of the beamforming technique utilized in the prior art and in the acoustic leak detection system of the invention, respectively.

The passive acoustic tomography beamformer 94 (see FIG. 7) uses an array of sensors to measure the three-dimensional noise field in the volume of interest. The absolute noise intensity is measured at each nodal point. One or more sensors in the array is calibrated to provide an absolute measurement of the total noise intensity at the sensor location. The coherent noise reaching the array sensors is then related back to this reference level to produce absolute intensity measurements for each nodal point in the field. The sensors are spatially located around the volume of interest with a geometry which produces an optimum array gain at each point in the nodal mesh. With careful placement, the variation in array gain across the volume can be minimized, or alternatively optimized to provide the highest array gain at specific locations of most importance. The array gain at each nodal point is calculated from the sensor array geometric and the location of the nodal point. The intensity at each nodal point is corrected for actual array gain. A simple time-delay beamformer is shown in FIG. 8A. The three delays D1, D2 and D3 for three array sensors at locations a, b and c can be used to focus the array onto location L. In a practical system, ghost images of any noise source at location L will appear at any interceptions of the hyperbolae passing through the sensor locations. The intensity of these ghost images compared to the noise intensity at the true source falls rapidly as the number of sensors in the array increases. Experience indicates that arrays containing a minimum of eight sensors provide satisfactory suppression of ghost images.

The passive acoustic tomography beamformer has two other properties. The first is the ability to use either a Eulerian or Lagrangian coordinate nodal mesh; the second is the capability to "zoom" the array focus to provide more detailed measurements in any volumetric region of importance.

The Eulerian coordinate approach uses a nodal mesh whose spatial geometry is invariant with time, for example, the nodal mesh used in the steam generator acoustic leak detection system disclosed herein. In contrast, the Lagrangian mesh uses a nodal mesh with a geometric coordinate system that can change with time, for example, the nodal mesh can be rotated in synchronization with a propellor or rotor blade being tested in a wind tunnel. This provides continuous measurements from the same location on a moving volume over time.

Figure 8B:
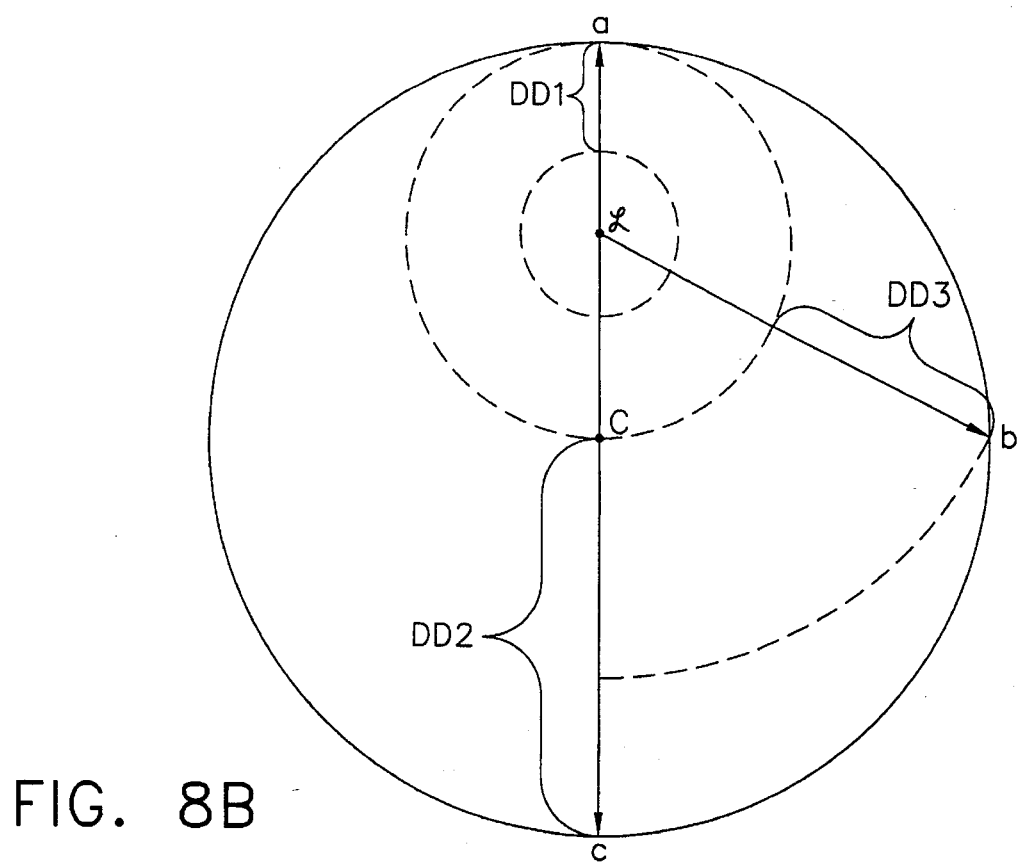

The beamformer in accordance with the invention also has zoom capability. The simplified beamformer shown in FIG. 8B illustrates this zooming concept. The three delays (DD1, DD2 and DD3) allow the beamformer to be focused onto a location L. The data from the sensors is digitized and stored in a memory and then accessed sequentially for calculation of nodal noise intensity. Not every data point is used to obtain the intensity at a nodal point; several data points are skipped to provide data at appropriate delay times for each sensor's data to be used correctly in nodal focusing. Zooming (or changing the nodal geometry) is accomplished in two steps. The first step will alter the signal capture synchronization so that delays are added to each sensor signal (DD1, DD2 and DD3), or alternatively a programmable delay will be set on each data input. (This assumes a datum bandwidth sample rate.) This effectively shifts the center of the nodal mesh to the point L from the original point C. The next step is to alter the data sampling rate, by altering the clocking frequency of the A/D converter. This effectively reduces or increases the mesh size in the ratio of sampling rate to datum rate. The software algorithm will use a fixed reference set of nodal mesh points, and the effective area mapped is reduced. Alternatively, the number of nodal points can be changed to cover a larger or smaller area depending upon the application. In the limit, the beamforming subsystem can be focused onto a relatively small area or single point for continuous monitoring. In an automatic location and monitoring application the focal point can also be automatically detected, and then changed to follow movement or other changes in the source characteristic.

The important parameters in designing a beamformer for real-time detection in an LMFBR steam generator include: (a) the number of focal points, or bins, that will be examined at each axial plane of the vessel; (b) the number of axial planes along the vessel length; (c) the maximum delay time required to phase the signals, or beamform the sensor array; and (d) the number of estimates required before making a decision on the probability that a leak exists.

The first two parameters are defined by the acoustic width (or signal bandwidth) of the sodium-water reaction. Experimental results indicate that a grid spacing of about 12 cm is required.

The number of bins, or focal points, in each plane of the steam generator increases as the square of the vessel diameter. In a 1.2-m (4-ft) diameter vessel the number of bins is approximately 50, increasing to 500 for a vessel of 3.7-m (12-ft) diameter. The number of planes is calculated from the separation of 12 cm and the vessel length, and a vessel length of about 22 m (70 ft) results in approximately 200 planes.

The eight signals from the accelerometers are normalized to the mean power of the signals to avoid complex algorithm data manipulation. After normalization of each signal, the beamformer delays each an amount corresponding to differences in propagation times from the focal point to each accelerometer. The phased data is used to obtain the acoustic power of the focal point. The coherent power for each bin is obtained from the ratio:

(Phased Power–Unphased Power)/Unphased Power

The value of this ratio is given the name CORCO. Acoustic pressure data by their nature will not have a time-consistent amplitude. It is necessary to accumulate a number of coherent power estimates before making a decision on the probability that the CORCO value is unusually (statistically) high. A high localized coherent power is assumed to be a leak site within the vessel volume.

The number of estimates, or samples, of CORCO required depends upon the relative strength of the leak noise compared to the general background noise. A large leak will consistently supply relatively high values of CORCO, and so a decision can be made after accumulating a relatively small number of samples. Conversely, a small leak will require a large number of samples. The number of samples required are governed by statistical laws.

The time domain beamformer accumulates frames of data, typically for periods between 51 msec and 0.1 sec for each channel. This data is then stored in a buffer as an array which can be accessed by the beamformer. Beamforming is performed by vectoring into the accumulated data array at specific locations corresponding to the relative time delays for each of the eight original signals. This vectoring can be done every fourth data point for each bin, each increment providing an independent estimate of the signal power from that location. Similar data vectoring and accumulation must be performed for each focal point in the plane. While this data manipulation is underway, a second set of signals is captured and stored in a second data buffer. The objective is to complete all data manipulations within the data collection time, and then switch to the second data array and repeat the process.

Figure 9:
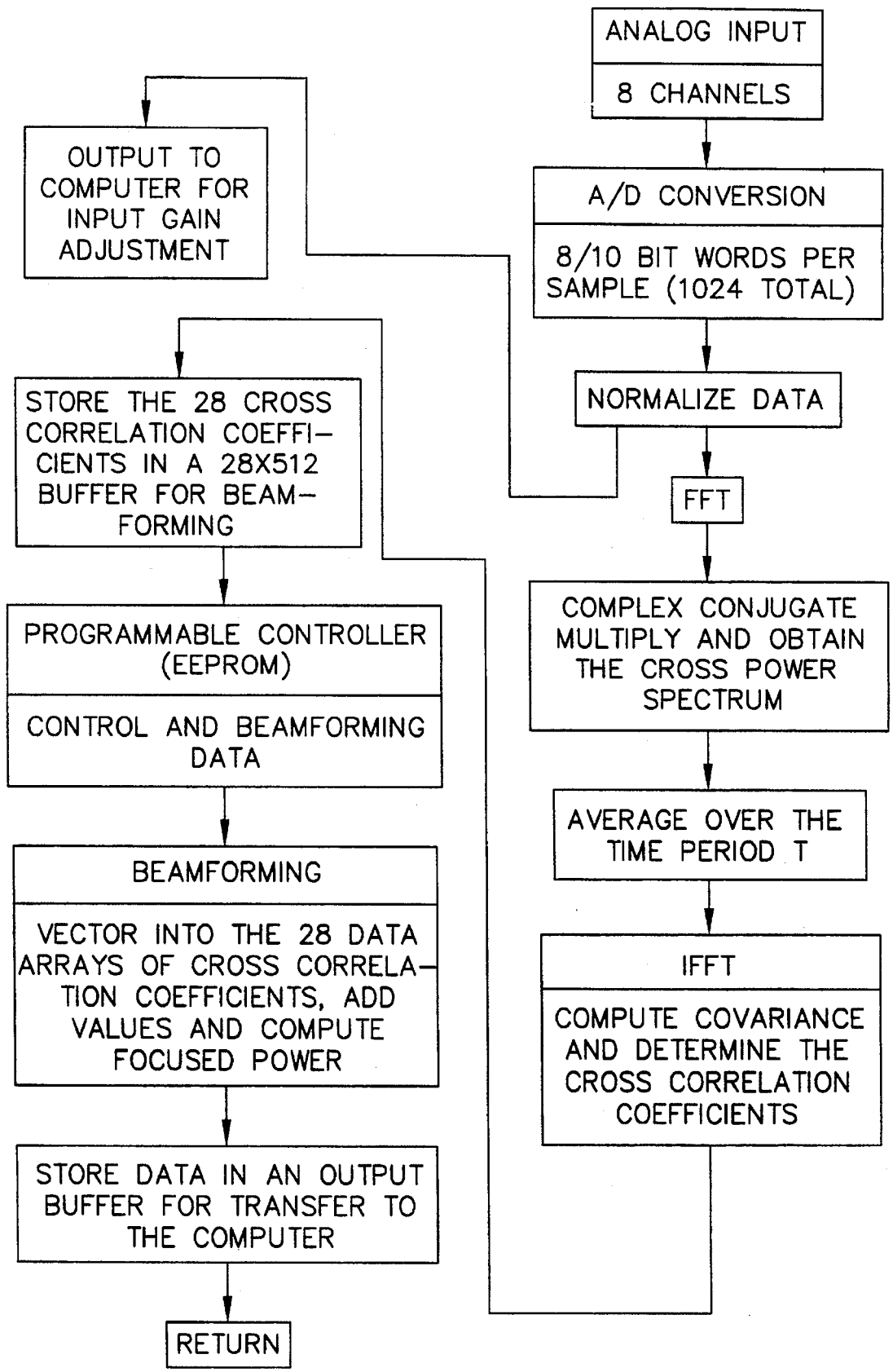
FIG. 9 is a flowchart showing the sequence of steps during the beamforming process utilized in the acoustic leak detection system in the invention.

Frequency domain beamforming is the preferred technique for performing real-time acoustic monitoring in accordance with the invention. Changing from the time domain to the frequency domain is accomplished by mathematical manipulation of the digitized data from the eight contiguous sensors. The following steps are involved (see FIG. 9):

(a) Eight independent, parallel channels of analog voltage carry the inputs to the frequency domain beamformer. Each analog voltage is 10 volts peak-to-peak, 500–30 kHz, 50 ohms.

(b) The signals from the eight analog channels are simultaneously digitized at a rate of 80 kHz or more. Each word is at least 10 bits in length. For each channel 1024 successive samples are digitized.

(c) The variance of the input data is computed. The data is normalized by dividing each value by the variance. The final result is adjusted to fit within a digital range of ±350 (base 10). The values of the eight rms voltage levels are output to the host computer to provide the proper gain settings for the next data pass.

(d) Each normalized data value is transformed into its frequency components using a forward Fast Fourier Transform (FFT). Each of the transformed signals has a single frequency and known amplitude.

(e) Individual frequency components are complex conjugate multiplied to determine the cross-power spectrum. In other words, the signals are manipulated so that signal 1 data is multiplied by signal 2 data, 1×, 1×4, . . . , 7×8. This forms the 28 data arrays of the cross-power between any two sensor signals as a function of frequency.

(f) The data for each cross-power value is averaged for a time period T (typically 51 msec), corresponding to the minimum time period necessary to check for alarm conditions.

(g) The inverse FFT of the average cross-power spectrum is taken. This gives the covariance for each of the 28 signal pairs. The cross-correlation coefficient is obtained by dividing the covariance by the mean amplitude of the original data.

(h) The result is a data array of 28 sets of cross-correlation coefficient data. The cross-correlation coefficient is a measure of the similarity of the two original signals when one is held stationary and the other is time delayed. In the current example, the coefficient is calculated and stored for 512 separate delay times. These delay times cover those required for beamforming onto any location in the current plane. The 512 time delay steps are sufficiently small that interpolation between them is not necessary. The data in this beamforming buffer will be acted upon by the programmable controller.

(i) The potential for a leak to exist at a specific location is obtained by vectoring into these 28 data arrays for all possible accelerometer couplets (at the appropriate differential delay time between the paths from the location to the sensors). The value of CORCO is the average power (ratioed to background power) of the 28 vectored values.

Current digital signal processing (DSP) hardware has many data manipulation functions embedded in hardware to increase computational speed in calculating standard functions such as Fast Fourier Transforms (FFT). Lower cost and DSP function integration in hardware has resulted in a beamforming subsystem design with multi-processors, parallel processing and multi-tasking. The design uses dedicated DSP embedded processors to perform many of the array data manipulations. The beamforming subsystem has complementary computer simulation programs in the host computer which can simulate additional sensors, restructuring of data processing or enhancements to the array processing. Initially the simulation would be run independently of the continuous operation of the mapping process. When the simulation is satisfactory, it can then use real-time data broadcast from the sensor array (FIFO output), and finally mirror the mapping process and predict the beamforming subsystem output. When the simulated system is satisfactory, the DSP processors can be automatically programmed by the simulation software to the new configuration. This on-line simulation can include simulation of the neural network/fuzzy logic subsystems described below, and reprogramming of the embedded association (or inference) engines used in these subsystems.

The beamforming subsystem has significant enhancements in diagnostic capability which will enhance system, subsystem, and component reliability. The Smart Access feature mentioned earlier provides both current and archival data and information on component and subcomponent performance. Further enhancement is provided by use of the integrated simulator capability described above. This provides an independent assessment of the current performance of the system when compared to the original performance predictions of the simulation model. The system performance model can also be simulated in a neural network system. The neural network would be trained initially using the simulator, and then upgraded by actual plant performance.

The neural network preprocessor is used as an initial leak indicator for the IALDS. The network is trained to detect a leak by recognizing discriminating patterns of data from an array of sensor inputs to the network. This network is trained initially using data from the integrated simulation software described earlier and then its recognition capability is upgraded by actual plant performance. Using a simulation allows the network to be exposed to a wide range of patterns representing a wide variety of operating conditions and leak characteristics. The neural network is trained and tested using the simulated data to ensure that it is not only robust and stable, but has the flexibility and capability to extrapolate beyond the training base. This means it will have the capability to recognize and indicate the presence of a leak (using either the low frequency or high frequency bands) that is different from the training examples. Although it may take an extended length of time to train the neural network to recognize the leak, the trained network performs the actual detection assessment within a fraction of a second.

Another feature of the neural network leak detection system and IALDS preprocessor is the capability to be trained to one level of detection probability (say 90% probability of detection and 10% probability of error) and then test the input data to a lower level of detection probability (say 60% probability of detection and 40% probability of error). In effect the neural network preprocessor is a detection system with a variable detection sensitivity. The neural network can be opened to a greater possibility of indicating a leak (is a more sensitive detector) but with a corresponding decrease in being correct (higher probability of false indication). Since several preprocessors are simultaneously monitoring different axial regions, two or more may receive a sufficiently strong signal to produce a leak indication at this degree of detection sensitivity. If the detection capability is made broad and a leak is indicated, the fuzzy logic part of the preprocessor can immediately tighten the detection capability to confirm a real indication. If an indication is still given as the detection capability is tightened, the fuzzy logic expert subsystem will cause the system to scan the appropriate region of the vessel with its increased detection sensitivity and very low false alarm rate.

This system has been described as it would be used in detection of a leak in a liquid metal steam generator. The same system has many other potential applications, for example, in medical, chemical and process plants for fault detection, performance monitoring and diagnosis. The system described can have many optional features to extend its utility for performance monitoring, diagnosis and training functions. The electrical signal voltages from the transducers may be presented to an operator for audible level, response monitoring, and/or human interpretation. As an example, with the system applied to a steam generator vessel, the array of transducers covers the surface of the vessel. Sound characteristics detected below a liquid/gas surface differ markedly from the acoustic energy transferred to sensors above the interface. Thus, knowing the identity and location of each sensor, the liquid level in such a vessel may be readily deduced. The same sensor output voltages permit detection of loose parts, pump and valve operations, pending failures in components moving the fluid, the monitoring of anomalous sounds in the vicinity of the monitored vessel, etc.

It is anticipated an integrated simulation would be developed to provide the ALMR designers with an interactive system design tool. This would allow advanced DSP hardware to speed up the interface with the designer and provide real-time optimization studies. The simulation can also accommodate real-time input from experimental rigs during system verification and validation activities. The same simulation becomes a powerful tool during ALMR licensing activities, and ultimately a training simulator for preparing reactor operators.

Further, many faults in process plant components are accompanied by a localized noise source. Similarly the same technology allows noise source generators to be identified even when masked by a reverberant field, such as mapping noise generation by models in a wind tunnel to ascertain operational or performance characteristics of components or structures within a highly reverberant field.

The preferred embodiment has been disclosed for the purpose of illustration. Variations and modifications of those embodiments will be readily apparent to engineers of ordinary skill in the arts of digital signal processing, array processing, artificial intelligence, or acoustic and ultrasonic detection. All such variations and modifications are intended to be encompassed by the claims appended hereto.

We claim:

1. An apparatus for detecting an anomaly in a monitored volume, comprising:

a plurality of transducers coupled to a respective plurality of localized portions of said monitored volume, each of said transducers outputting a respective analog electrical signal having a low-frequency component which is a function of the vibrational displacement of said localized portions of said monitored volume;

means for converting said respective analog electrical signals into respective digital electrical signals;

means for multiplexing said respective digital electrical signals from said respective transducers; and neural network processing means for recognizing a predetermined pattern in the digital electrical signals of any transducer having said predetermined pattern masked by background noise, said predetermined pattern reflecting a possible anomaly in said monitored volume.

2. The apparatus as defined in claim 1, wherein said analog electrical signals output by said transducers have high-frequency components which are a function of the ultrasonic waves propagating through said respective one of said plurality of localized portions of said monitored volume, further comprising a plurality of means for splitting the respective outputs of said plurality of transducers into said low- and high-frequency components.

3. The apparatus as defined in claim 2, wherein said neural network processing means comprises a first neural network processor for recognizing predetermined patterns in the digital electrical signals corresponding to said low-frequency components of said analog electrical signals and a second neural network processor for recognizing predetermined patterns in the digital electrical signals corresponding to said high-frequency components of said analog electrical signals.

4. The apparatus as defined in claim 3, further comprising chemical sensor means for monitoring for the presence in said monitored volume of a chemical compound produced when an anomaly of a predetermined kind is present in said monitored volume, and fuzzy logic anomaly detection processing means coupled to receive the outputs of said first and second neural network processors and said chemical sensor means, said fuzzy logic anomaly detection processing means being programmed in accordance with a first set of fuzzy logic rules to output predetermined commands in response to a combination of inputs thereto which indicate an anomaly, said inputs including at least said outputs of said first and second neural network processors and said chemical sensor means.

5. The apparatus as defined in claim 4, further comprising beamforming means for monitoring a selected set of transducers in the probable location of said indicated anomaly in response to said predetermined commands from said fuzzy logic anomaly detection processing means.

6. The apparatus as defined in claim 5, further comprising fuzzy logic interface processing means for controlling the operating conditions within said monitored volume by applying a second set of fuzzy logic rules to data output by said beamforming means as the result of said monitoring of said selected set of transducers and data output by said fuzzy logic anomaly detection processing means.

7. The apparatus as defined in claim 6, wherein said monitored volume is the outer shell of a sodium-heated steam generator, and said fuzzy logic interface processing means reduces the power being produced by said steam generator in response to inputs thereto indicating an anomaly inside said monitored volume.

8. The apparatus as defined in claim 3, wherein said monitored volume is a vessel having a wall, and each of said transducers comprises an acoustic transducer, further comprising a plurality of rigid attachment means, each of said rigid attachment means coupling a respective one of said plurality of acoustic transducers to the external surface of a respective one of a plurality of localized portions of said vessel wall lying along a helix.

9. The apparatus as defined in claim 3, further comprising fuzzy logic anomaly detection processing means coupled to receive the outputs of said first and second neural network processors, said fuzzy logic defect detection processing means being programmed in accordance with a first set of fuzzy logic rules to output predetermined commands in response to a combination of inputs thereto which indicate an anomaly, said inputs including at least said outputs of said first and second neural network processors.

10. The apparatus as defined in claim 9, further comprising beamforming means for monitoring a selected set of transducers in the probable location of said indicated anomaly in response to said predetermined commands from said fuzzy logic anomaly detection processing means.

11. The apparatus as defined in claim 9, wherein said analog-to-digital converting means have a changeable sampling rate.

12. The apparatus as defined in claim 10, further comprising fuzzy logic interface processing means for controlling operating conditions within said monitored volume by applying a second set of fuzzy logic rules to data output by said beamforming means as the result of said monitoring of said selected set of transducers and data output by said fuzzy logic anomaly detection processing means.

13. A method for preventing damage caused by an anomaly in a monitored volume, comprising the steps of:

detecting acoustic waves produced by said anomaly at a plurality of locations in said monitored volume;

detecting the amount of a chemical compound at a location inside said monitored volume, said chemical compound being produced when an anomaly of a predetermined kind is present in said monitored volume;

applying a set of fuzzy logic rules to at least the data acquired by said detecting steps; and controlling the operating conditions within said monitored volume in dependence on the results of said step of applying fuzzy logic rules to at least said acquired data.

14. The method as defined in claim 13, wherein said monitored volume is the outer shell of a sodium-heated steam generator, the power produced by said steam generator being reduced in response to results of said step of applying fuzzy logic rules to at least said acquired data indicating an anomaly inside said monitored volume.

15. An apparatus for detecting an anomaly in a monitored volume, comprising:

a plurality of transducers coupled to a respective plurality of localized portions of said monitored volume, each of said transducers outputting a respective analog electrical signal having a low-frequency component which is a function of the vibrational displacement of said localized portions of said monitored volume;

means for converting said respective analog electrical signals into respective digital electrical signals;

beamforming means for combining said digital electrical signals corresponding to acoustic waves originating from a predetermined unit volume inside said monitored volume at the same instant in time; and fuzzy logic processing means for controlling the operating conditions inside said vessel by applying a set of fuzzy logic rules to at least the data output by said beamforming means.

16. The apparatus as defined in claim 15, wherein said analog-to-digital converting means have a changeable sampling rate.

17. The apparatus as defined in claim 15, wherein said monitored volume is the outer shell of a sodium-heated steam generator, and said fuzzy logic processing means reduces the power being produced by said steam generator in response to inputs thereto indicating an anomaly inside said monitored volume.

18. A method for locating an anomaly within a monitored volume, comprising the step of:

coupling a plurality of transducers to a plurality of localized portions of said monitored volume so that each of said plurality of transducers outputs an analog electrical signal having a low-frequency component which is a function of the vibrational displacement of a respective one of said plurality of localized portions of said monitored volume and a high-frequency component which is a function of the vibrational/ultrasonic waves propagating through said respective one of said plurality of localized portions of said monitored volume;

converting said respective analog electrical signal components into respective digital electrical signals;

processing said digital electrical signals through a neural network trained to recognize predetermined patterns in said respective digital electrical signals, said predetermined patterns reflecting possible anomalies within said monitored volume;

monitoring for the presence in said monitored volume of a chemical compound produced when an anomaly of a predetermined kind is present in said monitored volume; and processing the results of said neural network processing and said monitoring in accordance with a first set of fuzzy logic rules to output predetermined commands in response to results indicating an anomaly.

19. The method as defined in claim 18, further comprising the step of beamforming the low-frequency components of a subset of said plurality of transducers nearest to the probable location of said indicated anomaly in response to said predetermined commands.

20. The method as defined in claim 19, further comprising the step of controlling the operating conditions inside said monitored volume by applying a second set of fuzzy logic rules to at least the result of said beamforming and the results of said processing in accordance with said first set of fuzzy logic rules.

* * * * *